(12) United States Patent
Cunanan et al.

(10) Patent No.: US 9,095,430 B2
(45) Date of Patent: Aug. 4, 2015

(54) BIOMATERIALS WITH ENHANCED PROPERTIES AND DEVICES MADE THEREFROM

(75) Inventors: Crystal M. Cunanan, Mission Viejo, CA (US); John Joseph Higgins, Palmerston North (NZ); Saroja Nagaraj Guradzada, Palmerston North (NZ)

(73) Assignee: SOUTHERN LIGHTS VENTURES (2002) LIMITED (NZ)

( * ) Notice: Subject to any disclaimer, the term of this patent is extended or adjusted under 35 U.S.C. 154(b) by 0 days.

(21) Appl. No.: 13/217,234

(22) Filed: Aug. 24, 2011

(65) Prior Publication Data
US 2012/0059487 A1    Mar. 8, 2012

Related U.S. Application Data

(60) Provisional application No. 61/376,627, filed on Aug. 24, 2010.

(51) Int. Cl.
*A61F 2/02*     (2006.01)
*A61F 2/24*     (2006.01)
(Continued)

(52) U.S. Cl.
CPC .............. *A61F 2/2412* (2013.01); *A61F 2/2427* (2013.01); *A61L 27/3604* (2013.01);
(Continued)

(58) Field of Classification Search
CPC . A61F 2/2412; A61F 2/2427; A61L 27/3604; A61L 27/507; A61L 27/36; A61L 27/3625; A61L 31/005; A61L 2430/40; A61L 2430/20; A61K 35/34; Y10S 623/918
See application file for complete search history.

(56) References Cited

U.S. PATENT DOCUMENTS

| | | | |
|---|---|---|---|
| 4,340,977 A | 7/1982 | Brownlee et al. | |
| 4,553,974 A | 11/1985 | Dewanjee | |

(Continued)

FOREIGN PATENT DOCUMENTS

| | | | |
|---|---|---|---|
| WO | WO 2011/072084 A3 | 6/2011 | |
| WO | PCT US2011/049027 | 2/2012 | |

OTHER PUBLICATIONS

Cuananan C M et al (2001). *Tissue characterisation and calcification potential of commercial bioprosthetic heart valves*. The Annals of Thoracic Surgery 71:417-421.

(Continued)

*Primary Examiner* — Julian W Woo
*Assistant Examiner* — Shaun L David
(74) *Attorney, Agent, or Firm* — Kurt T. Mulville; VLP Law Group LLP

(57) ABSTRACT

Biomaterials with enhanced properties such as improved strength, flexibility, durability and reduced thickness are useful in the fabrication of biomedical devices, particularly those subjected to continuous or non-continuous loads where repeated flexibility and long-term durability are required. These enhanced properties can be attributed to elevated levels of elastin, altered collagen types, and other biochemical changes which contribute to these enhanced properties. Examples of devices which would be improved by use of such tissue include heart valves, including percutaneous heart valves, and vascular grafts, patches and the like. Such enhanced materials can be sourced from specific populations of animals, such as neonatal calves, or in range-fed adult cattle, or can be fabricated or created from cell populations exhibiting such properties. In one embodiment, glutaraldehyde-fixed neonatal pericardial tissue is used to create leaflets in a percutaneous heart valve, and may be used without chemical fixation, with or without processes to remove residual cellular membranes, and utilized as a scaffold material for tissue engineering.

11 Claims, 18 Drawing Sheets

(51) Int. Cl.
*A61L 27/36* (2006.01)
*A61L 27/50* (2006.01)
*A61L 31/00* (2006.01)
*A61K 35/34* (2015.01)

(52) U.S. Cl.
CPC ............ *A61L27/507* (2013.01); *A61L 31/005* (2013.01); *A61K 35/34* (2013.01); *A61L 2430/40* (2013.01); *Y10S 623/918* (2013.01)

(56) References Cited

U.S. PATENT DOCUMENTS

| | | | |
|---|---|---|---|
| 5,002,566 | A | 3/1991 | Carpentier et al. |
| 5,716,399 | A * | 2/1998 | Love .............................. 128/898 |
| 5,843,182 | A | 12/1998 | Goldstein |
| 5,931,969 | A | 8/1999 | Carpentier et al. |
| 6,210,957 | B1 | 4/2001 | Carpentier et al. |
| 6,652,583 | B2 | 11/2003 | Hopkins et al. |
| 7,422,607 | B2 | 9/2008 | Oviatt et al. |
| RE40,570 | E | 11/2008 | Carpentier et al. |
| 7,658,706 | B2 | 2/2010 | Squillace |
| 7,919,112 | B2 | 4/2011 | Pathak et al. |
| 7,922,764 | B2 | 4/2011 | Gordy et al. |
| 7,972,376 | B1 | 7/2011 | Dove et al. |
| 2007/0254005 | A1* | 11/2007 | Pathak et al. ................. 424/423 |
| 2009/0248143 | A1 | 10/2009 | Laham |
| 2011/0224779 | A1* | 9/2011 | Schankereli ................. 623/1.24 |

OTHER PUBLICATIONS

Ghanbari H et al (2008) *Percutaneous heart valve replacement: An update.* Trends in Cardiovascular Medicine 18:117-125.
Khor E (1997) *Review: Methods for the treatment of collagenous tissues for bioprostheses* Biomaterials 18:95-105.
Schmidt C E and Baier J M (2000) *Acellular vascular tissues: natural biomaterials for tissue repair and tissue engineering* Biomaterials 21:2215-2231.
Simionescu A et al (1991) *Lysine-enhanced glutaraldehyde crosslinking of collagenous biomaterials* Journal of Biomedical Materials Research 25:1495-1505.
Simionescu D T (2004) *Prevention of calcification in bioprosthetic heart valves: challenges and perspectives* Expert Opinion in Biological Therapy 4(12):1971-1985.
Simionescu D T (2006) *Artificial heart valves* Wiley Encyclopaedia of Biomedical Engineering, John Wiley & Sons Inc.
Tedder M E et al (2009) *Stabilized collagen scaffolds for heart valve tissue engineering* Tissue Engineering part A 15(6):1257-1268.
Naimark et al., "Correlation of structure and viscoelastic properties in the pericardia of four mammalian special", 1992 the American Physiological Society, H1095-H1106, 12 pgs.
Paez et al., "Comparison of elasticities of components of a cardiac bioprosthesis leaflet", Journal of Biomedical Materials Research, vol. 30, 47-52 (1996) 6 pgs.
Paez et al., "A new method for selecting calf pericardium for use in cardiac bioprostheses on the basis of morphological and mechanical criteria", Journal of Materials Science: Materials in Medicine 12 (2001) 655-671, 9 pgs.
Paez et al., "Durability of a cardiac valve leaflet made of calf pericardium: Fatigue and energy consumption", Wiley InterScience, , www.interscience.wiley.com, Apr. 4, 2006, 12 pgs.
Almine et al., "Elastin-based materials", Chemical Society Reviews, 2010, 39, 3371-3379, May 7, 2010, http://pubs.rse.org, 10 pgs.
Khor, Eugene, "Methods for the treatment of collagenous tissues for bioprostheses", Biomaterials 1997, vol. 18, No. 2, p. 95-105, 11 pgs.
Paez et al., "Uniaxial and Biaxial Tensile Strength of Calf Pericardium Used in the Construction of Bioprostheses: Biomaterial Selection Criteria", Journal of Biomaterials Applications, vol. 15, Jul. 2000, p. 47-64, 18 pgs.
Paez et al., "Influence of the Selection of the Suture Material on the Mechanical Behavior of a Biomaterial to be Employed in the Construction of Implants. Part 1: Calf Pericardium", Journal of Biomaterials Applications, vol. 16, Jul. 2001, p. 47-67, 22 pgs.
Paez et al., "Resistance and Stability of a New Method for Bonding Biological Materials Using Sutures and Biological Adhesives", Journal of Biomaterials Applications, vol. 19, Jan. 2005, p. 215-236, 22 pgs.
Rnjak et al., "Severe Burn Injuries and the Role of Elastin in the Design of Dermal Substitutes", Tissue Engineering: Part B, vol. 17, No. 2, 2011, p. 81-91, 11 pgs.
San Martin et al., "Selection and interaction of biomaterials used in the construction of cardiac bioprostheses", c 1998 John Wiley & Sons, Inc. CCC 0021-9305/98/040568-07, p. 568-574, 7 pgs.
Zioupos et al., "Mechanics of native bovine pericardium", Biomaterials 1994, vol. 15, No. 5, p. 374-382, 9 pgs.
Aldous et al., "Differences in collagen cross-linking between the four valves of the bovine heart: a possible role in adaptation to mechanical fatigue", Am J Physiol Heart Circ Physiol 196, ajpheart.physiology.org, p. H1898-1900, 10 pgs.
Bashey et al., "Characterization of Pepsin-Solubilized Bovine Heart-Valve Collagen", Biochem. J. (1978) 173, pp. 885-894, 10 pgs.
Carta et al., "Discrete contributions of elastic fiber components to arterial development and mechanical compliance", NIH Author Manuscript, published as: Arterioscler Thromb Vasc Biol. Dec. 2009, 17 pgs.
Cole et al., "Collagen composition of normal and myxomatous human mitral heart valves", Biochem. J. (1984) 219, pp. 451-460, 10 pgs.
Jimenez et al., "Solubilization of Bovine Heart-Valve Collagen", Biochem. J. (1978) 173, pp. 337-340, 4 pgs.
Wagenseil, et al., "Vascular Extracellular Matrix and Arterial Mechanics", NIH Author Manuscript, published as: Physiol Rev. Jul. 2009, 57 pgs.
Schoen et al., Calcification of Bovine Pericardium Used in Cardiac Valve Bioprostheses, Am J Pathol 1986, vol. 123, pp. 134-145, 12 pgs.
EP, Communication pursuant to Article 94(3) EPC, Application No. 11 757 704.9, Mar. 5, 2014.
NZ, New Zealand $2^{nd}$ Examination Report. Application No. 607498, Feb. 5, 2015.
NZ, New Zealand $1^{st}$ Examination Report, Application No. 703981, Feb. 5, 2015.

* cited by examiner

BIOMATERIALS WITH ENHANCED PROPERTIES AND DEVICES MADE THEREFROM

This application claims the benefit of U.S. Provisional Application No. 61/376,627 filed Aug. 24, 2010, which application is incorporated herein by reference.

FIELD

The subject matter described herein relates generally to new biomaterials with enhanced properties, such as improved strength, flexibility, durability and reduced thickness, where these enhanced properties enable the creation of new and improved medical devices, such as small-profile percutaneous heart valves, thin, flexible patches for repair, and tissue engineering scaffolds with enhanced elasticity and durability. These enhanced properties are due to compositional differences between the embodiments described herein and the prior art, including elevated elastin levels, altered collagen types, and other biochemical differences which contribute to enhanced strength, flexibility, durability and reduced thickness.

BACKGROUND

Current medical devices fabricated from prior art biological tissues tend to suffer from various limitations, due in part to the limited properties of the materials from which they are fabricated. Materials with improved properties would enable development of new and enhanced devices which are not possible with biomaterials used today. For example, percutaneous heart valves are under development to enable minimally-invasive replacement of damaged or diseased heart valves. A critical dimension of the percutaneous technology is to be able to deliver the device in a small diameter catheter so that it can be threaded through the arterial system and positioned within the heart before expansion. As described by Chiam and Ruiz, *Percutaneous Transcatheter Aortic Valve Implantation*, Journal of American College of Cardiovascular Interventions, volume 1, pp 341-50, 2008, early percutaneous heart valves were 25F (French, or about 8.4 mm in diameter), which compares poorly with current catheter-based interventions, such as stents and the like, which are 4-6F (1.4-2.0 mm) in size. Indeed, Kroger et al, in *Diameter of occluded superficial femoral arteries limits percutaneous recanalization*, Journal of Endovascular Therapeutics, volume 9, pp 369-74, 2002, report that patients with peripheral arterial disease have an average femoral artery diameter of 4.5 mm in diseased vessels and a vessel diameter of 5.7 mm in non-diseased arteries. Therefore to treat patients without vessel disease, a percutaneous valve needs to be less than 5.7 mm in diameter, or less than 17F size. To treat patients with vessel disease, the compressed valve diameter should be less than 4.5 mm, which would require a 13F diameter valve. Since patients requiring heart valve replacement frequently have comorbidities such as vessel disease, a technology that cannot be introduced into a diseased vessel would fail to treat the majority of the patient population. As current stents are able to collapse to a 4-6F size, the limiting factor in the ability to provide this important new therapy to patients is the ability to reduce the collapsed size of the valve. Since it is already possible within the prior art technologies to create a stent which can meet the size criterion, the limiting factor is the tissue. Therefore, a tissue that is strong, durable, flexible and ultrathin, would be a material which would enable percutaneous valve technologies to develop the minimal profile size required to treat these patients.

In the area of soft tissue repair and orthopedics, new biomaterials which are strong, durable, flexible and thin are also needed. Currently extracellular matrix (ECM) graft materials are approved for augmentation or replacement of soft tissue structures, such as tendon and ligament repair, bladder and breast reconstruction, skin grafting, and general soft tissue reinforcement of defects in organ walls, such as abdominal and thoracic walls. As described by J H Yoder et al, *Nonlinear and anisotropic tensile properties of graft materials used in soft tissue applications*, Clinical Biomechanics, volume 25, pp 378-82, 2010, the available ECM materials have limits on the critical properties needed for these applications, including strength, flexibility, durability or thickness, and are, therefore, less ideal for the intended repairs. For example, many allogenic skin graft materials do not have the desired strength for high stress applications requiring long term durability. Acellularized porcine small intestine submucosa (SIS) is used for some applications, but requires many layers to be laminated together to provide sufficient tensile strength for repair. Unfortunately, laminating 4, 8 or 10 layers of SIS tissue yields a stiff resulting laminate with limited flexibility. Equine pericardium has desirable strength characteristics, but is unacceptably thick for some applications. Having access to ECM graft materials which are strong, durable, flexible and ultrathin would enable new and improved soft tissue repair and reconstruction devices to be fabricated without the inherent limitations of current technologies.

A third area where biomaterials with enhanced properties would enable the development of important new technologies is in the area of tissue engineering. Tissue engineering is defined as an interdisciplinary field that applies the principles of engineering and life sciences toward the development of biological substitutes that restore, maintain, or improve tissue function or a whole organ (R P Lanza, R Lander, W L Chick, editors, *Principles of Tissue Engineering*, Academic Press, 1997). Tissue engineering is a large and growing field of research, and covers diverse applications in the areas of the cardiovascular system (such as tissue engineered heart valves and vessels), the musculoskeletal system (tissue engineered bone, cartilage, connective tissues, tendons and ligaments), ophthalmology (such as tissue engineered cornea and other ocular tissues), the nervous system (such as in tissue engineered implants for repair of spinal cord defects or peripheral nervous tissue regeneration), periodontal and dental applications (tissue engineered bone, implants, and surrounding soft tissues), wound repair (tissue engineered skin, dermis, or connective tissues), endocrinology (such as tissue engineered pancreas and parathyroid), the gastrointestinal system (tissue engineered intestine and liver), and the kidney and genitourinary system. Tissue engineering became a field in its own right once scientists came to appreciate the importance of the extracellular matrix as a crucial determinant for enabling cellular cooperation in multicellular complexes to carry out their programs for cell division and differentiation. Eugene Bell quickly identified the value of acellular materials which could be implanted in the body as percursors of tissue replacements, and to have them recruit appropriate cells from neighboring tissues or circulating fluids, thereby enabling the reorganization and replacement of tissues and organs with the host's own cells, using the extracellular matrix material as a scaffold (*Principles of Tissue Engineering, foreword*, 1997). Another use of extracellular matrix materials in tissue engineering is to apply living cells to the scaffold material outside of the body, in a suitably designed bioreactor, where the cells can then proliferate and differentiate, remodeling the scaffold into the desired tissue or organ. Upon reaching a certain stage of maturity, the living cell-scaffold construct is implanted in the body to serve its intended function (Fred Schoen, ch 8, *Tissue Engineering in Biomaterials Science: An Introduction to Materials in Medicine,* 2nd edition, Elsevier Press, 2004). Regardless of the approach, the ECM scaffold is a critically important element in all tissue engineered constructs. Providing adequate strength, durability, and flexibility during the remodeling process is essential for successful incorporation of a tissue engineered replacement tissue or organ.

To-date, materials used as scaffolds in tissue engineering, primarily SIS tissue or biodegradable synthetic polymers, are severely limited in application because of the lack of strength and durability. Complicated pulsing or flowing bioreactors are currently utilized in an effort to stimulate production of ECM materials for strength, but these systems require complex equipment with long culturing times in order to generate tissues with some minimum mechanical strength. A frequent problem with biodegradable polymers is that they degrade faster than the cells can synthesize replacement matrix, resulting in mechanical failure. Materials which can be utilized in transplant as scaffolds and that do not require complex culturing conditions and that already contain the desired combination of strength, flexibility and composition would be a significant improvement over scaffold materials currently available. Tissue materials that are strong, durable, flexible and ultrathin would greatly enable the use of tissue engineering principles and concepts to the create of commercial products and therapies.

SUMMARY OF INVENTION

Embodiments provided herein are directed to new biomaterials with enhanced properties which will enable the development of new and improved medical devices. These properties of enhanced strength, durability, flexibility and reduced thickness are due, in part, to identification and selection of materials having an elevated elastin content. The biomaterials can be selected from natural sources of tissues, or can be constructed in the laboratory or in an animal model. The new biomaterials can be processed in a variety of ways to target selective needs of a particular device. In one embodiment, the biomaterial can be crosslinked with glutaraldehyde so that the tissue can be used as a leaflet material in a percutaneous bioprosthetic heart valve. Because the tissue is ultrathin, it can enable the packing of the valve to be reduced compared to existing technologies, for example, to 16 French (16F), or 5.3 mm in diameter, or less to enable low profile insertion of prosthetic valves. In another embodiment it could be crosslinked with a carbodiimide and sterilized for use in soft tissue reconstruction, as a patch, strip, or wrap. In another embodiment, the tissue is isolated from the donor animal, decellularized and disinfected to be used as a tissue, graft, transplant, or engineering scaffold, where the greater strength and elasticity of the material enables tissue engineered devices to be made which experience a high degree of flexure or working stress, such as in a heart valve leaflet or as a vascular graft.

Embodiments provided herein are also directed to a method of fabricating the new biomaterials, including sourcing from animals of a particular age or species, such as, e.g., New Zealand calves. As these tissues are composed primarily of collagen, the degradation of collagen with time is the primary mode of failure. If tissue could be selectively enriched, or identified as naturally enriched, in components that enhance the mechanical performance of the device and thus delay structural deterioration, improved devices could be produced which exhibit enhanced durability. Elastin is one such component—tissues with higher elastin content would exhibit improved flexibility, greater elasticity, and longer durability. Devices fabricated from such tissues would be more resistant to fatigue-related failure by reducing the mechanical stress on the tissues during use, thereby reducing the degradation rate of the collagen in the tissues. Elastin is a very hydrophobic molecule and contains about 30% glycine, arranged randomly along its chain. This is in marked contrast to fibrillar collagens, which also contain 30% glycine, but have a very ordered repeat structure to the glycine placement—every third amino acid is glycine, which allows the collagen molecule to curl into a helix shape. Because the glycines in elastin are arranged randomly, elastin does not form helices, but is rather amorphous. It acts like a spring, stretching out when stress is applied to it, and recoiling to its original shape when the stress is released. Elastin molecules slide over each other in a way that reduces shear stress, a critical type of stress that greatly fatigues tissues which are subject to repeated flexure and loading. Therefore tissues with higher elastin content can better withstand shear stress.

It has long been appreciated the importance of shear stress in the degeneration of bioprosthetic tissues, such as adult bovine pericardial tissue or porcine aortic valve isolations. Thubrikar et al, *Role of mechanical stress in calcification of aortic bioprosthetic valves,* Journal of Thoracic and Cardiovascular Surgery, volume 86, pp 115-25, 1983 noted early on in the development of replacement heart valves made from tissues that the highest stresses in tissues occurred in the areas of the greatest flexion of the leaflet. In the zone of flexion, typical bovine pericardial tissues demonstrate shear deformation. Not only did shear deformation lead to degeneration of the tissue matrix, but it also enhanced calcification in the region of flexion. The authors summarize that mechanical stresses initiate calcification by damaging the structural integrity of the leaflet tissue. Therefore, calcification of bioprostheses can be inhibited by reducing functional stresses through the modification of design and tissue properties. While the industry has focused on modification of designs as a means to reduce stresses on the tissue, and chemical treatments to inhibit calcification, no one has examined the possibility of reducing functional stresses through special selection of tissue properties and combinations throughout.

Tissues high in elastin exhibit great dimensional stability and have the ability to store mechanical energy. This feature is believed to be very important in the cardiovascular system, for example, where the elastic arteries serve as elastic reservoirs, enabling the arterial system to undergo large volume changes with little change in pressure. The large elastic arteries are capable of storing a portion of the stroke volume with each systole and discharging that volume with diastole. This phenomenon, known as the windkessel effect, helps to decrease the load on the heart and to optimize blood flow in the smaller arteries. In a review of the development of the vascular system J E Wagenseil et al, *Vascular extracellular matrix and arterial mechanics, Physiology Reviews,* volume 89, pp 957-89, 2009, report that elastin synthesis is maximum by Day 14 in mice, declining sharply by Day 30, and maintaining almost no synthesis thereafter. Therefore, these selected tissues are procured from an identified source having the desirable parameters disclosed herein. The parameters can be verified either in individual animals, tissue portions, or animal population or species. The tissues are removed surgically, treated with processes designed to enhance their use in transplants, and typically cut into sizes to fascilitate their use as grafts or other structures e.g. heart valve leaflets. Tissues harvested shortly after birth should contain maximal amounts of elastin.

Altered collagen types would also result in tissues with enhanced durability and fatigue resistance. Reduced collagen crosslinking and other proteins are other components of tissue which would be desirable to use in creating bioprosthetic devices with improved properties. Because of the juvenile or fetal nature of the tissues used to create these devices, the devices themselves not only perform better, but also exhibit enhanced healing, reduced scar formation, and reduced fibrosis, compared to current devices. This is partially due to the reduced immunogenicity of the juvenile and fetal tissues, thereby resulting in improved healing after implantation of the device.

Because juvenile and fetal tissues are less crosslinked compared to adult tissues, processing of these juvenile and fetal tissues can allow enhanced stabilization of the resulting constructs, as more crosslinking sites will be available for the stabilization chemistry in juvenile and fetal tissues compared to adult tissues. Processing conditions can also be more mild and gentle when preparing juvenile and fetal tissue compared to adult tissues, because of this reduced crosslinking.

For example, harsh chemical conditions and mechanical and sometimes enzymatic degradation are required to process adult cow skin or tendons into a collagen slurry, which can then be processed into a variety of coatings, sheets, devices and so forth. Processing juvenile or fetal skin or tendon, which is less crosslinked compared to adult skin or tendon, and has a less mature composition of collagens, can be done using less stringent conditions. Processing under less stringent conditions can create materials with reduced degradation, higher molecular weight, and in general enhanced properties compared to adult tissues. In some cases, more mild processing conditions may enable certain compounds to be generated that could not be created or isolated from adult tissues. Enzymes, growth factors, very high molecular weight proteoglycans, and other biomolecules are some of the compounds which would be degraded, inactivated, or completely destroyed by the more aggressive conditions required to process adult tissues. In one embodiment of the invention, the animals may be juvenile bovines, under 12 months of age. Even fetal tissues may be used, provided the tissues meet the criteria of strength, flexibility and are ultrathin. In another embodiment, adult animals may be used as the source of the tissue, but in order to provide the desired characteristics of strength and flexibility, these animals are free-range fed, rather than fed in a stationary hold pen such as a feed lot. Feed lot bovines are typically used as a source material for bovine pericardium today. In another embodiment, animals may be specifically bred or genetically controlled to provide tissues with greater flexibility and reduced thickness compared to current source animals. Even cells from such animals which are capable of producing these new materials may be utilized to create materials with enhanced properties through the application of cell and organ culturing techniques.

In another embodiment, specific tissues having defined characteristics are used as source materials for a variety of medical devices. The specific parameters that may individually or collectively be selected, include elastin, collagen type and content, pepsin digestion, tissue thickness and composition, and tissue modulus. The specific tissue parameters may quantitatively or qualitatively assessed and generally distinguish neonatal from adult pericardium by assessing biochemical composition or biomechanical properties. Specifically, biomechanical properties may be a proxy for composition of the elastin, collagen, or other parameters and may further be defined by the distribution in orientation of elastin and the collagen fiber bundle. As described in more detail below, the distribution of elastin and collagen within the selected tissues of the invention provides a superior biomechanical performance. Similarly, the composition and orientation of structural features of the tissues including elastin, collagen, extent of cross-linking and others, as measured, provide a basis for selecting, identifying, or testing improved tissue materials. Mechanical testing of the specific materials may be done as part of a protocol to select specific tissues during tissue processing, or may be a separate quality control criteria for establishing suitable tissues. Accordingly, mechanical testing can either be used as a selective criteria or to confirm that the perimeters described herein, such as elastin content and collagen type analysis are accurately identifying selected preferred tissues. Similarly, thicknesses of tissues are readily measured to identify tissue types that feature the preferred characteristics described herein. Notably, tissue type can be used to assess both strength relative to thickness, as well as absolute thickness, and strength relative to different biomechanical properties or contents. The age of desired tissue sources is both predictive and a selection criteria because the pericardia from young animals tends to exhibit the preferred characteristics described below.

Other systems, methods, features and advantages of the example embodiments will be or will become apparent to one with skill in the art upon examination of the following figures and detailed description.

BRIEF DESCRIPTION OF FIGURES

The details of the example embodiments, including structure and operation, may be gleaned in part by study of the accompanying figures, in which like reference numerals refer to like parts. The components in the figures are not necessarily to scale, emphasis instead being placed upon illustrating the principles of the invention. Moreover, all illustrations are intended to convey concepts, where relative sizes, shapes and other detailed attributes may be illustrated schematically rather than literally or precisely.

It should be noted that elements of similar structures or functions are generally represented by like reference numerals for illustrative purpose throughout the figures. It should also be noted that the figures are only intended to facilitate the description of the preferred embodiments.

DETAILED DESCRIPTION OF INVENTION

Each of the additional features and teachings disclosed below can be utilized separately or in conjunction with other features and teachings to provide new biomaterials with enhanced properties. Representative examples of the embodiments described herein, which examples utilize many of these additional features and teachings both separately and in combination, will now be described in further detail with reference to the attached drawings. This detailed description is merely intended to teach a person of skill in the art further details for practicing preferred aspects of the present teachings and is not intended to limit the scope of the invention. Therefore, combinations of features and steps disclosed in the following detail description may not be necessary to practice the invention in the broadest sense, and are instead taught merely to particularly describe representative examples of the present teachings.

Moreover, the various features of the representative examples and the dependent claims may be combined in ways that are not specifically and explicitly enumerated in order to provide additional useful embodiments of the present teachings. In addition, it is expressly noted that all features disclosed in the description and/or the claims are intended to be disclosed separately and independently from each other for the purpose of original disclosure, as well as for the purpose of restricting the claimed subject matter independent of the compositions of the features in the embodiments and/or the claims. It is also expressly noted that all value ranges or indications of groups of entities disclose every possible intermediate value or intermediate entity for the purpose of original disclosure, as well as for the purpose of restricting the claimed subject matter.

Figure 1:
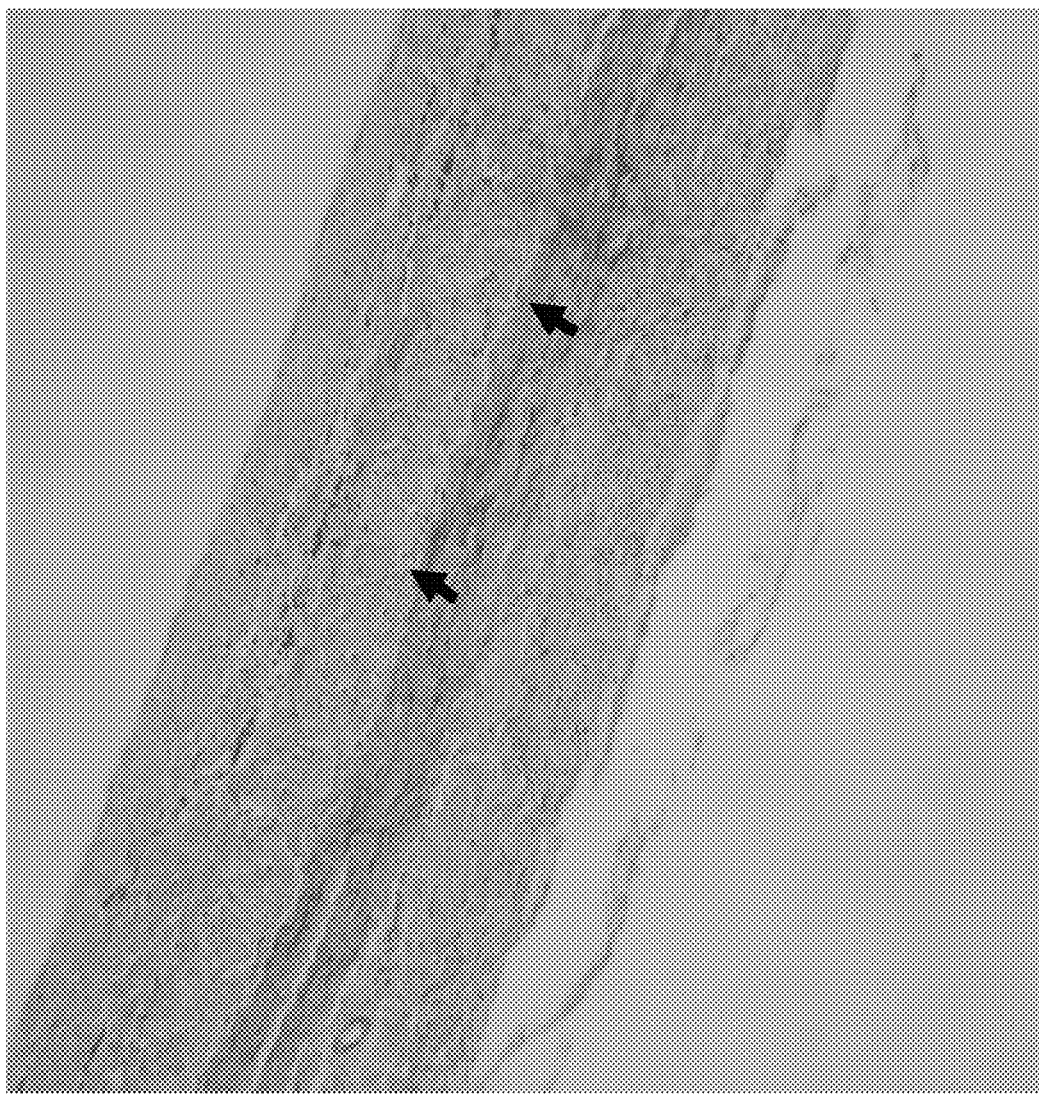
FIG. 1 is a histological cross-section of a neonatal bovine pericardial tissue stained for elastin exhibiting the desired characteristics of elevated elastin. Elastin stains darkly and is highlighted with the arrowheads.

Embodiments provided herein are directed to new biomaterials with enhanced properties such as strength, durability, flexibility, and reduced thickness which can be used to create new or improved medical devices. Unlike prior art tissues, the embodiments described herein are tissues with increased levels of elastin, improved collagen content and characteristics thereby yielding tissues with greater flexibility, elasticity, and durability. An exemplary embodiment includes the use of neonatal tissue, harvested from juvenile cows, less than one year old, less than 6 months old, less than 3 months old and preferably less than 30 days old. When the pericardia from such animals is isolated and prepared for histological processing, paraffin embedding, and staining with elastin stain, the tissue is found to contain extensive amounts of elastin, as seen in FIG. 1. Elastin is seen to stain darkly and is highlighted with arrowheads. Taken together with the other properties of this invention, such as collagen content reduced thickness, the use of neonatal bovine pericardial tissues will improve the performance of transplanted tissues, in a range of physical and biochemical characteristics including grafts and heart valve bioprostheses, including enhanced strength, durability and flexibility.

Figure 2:
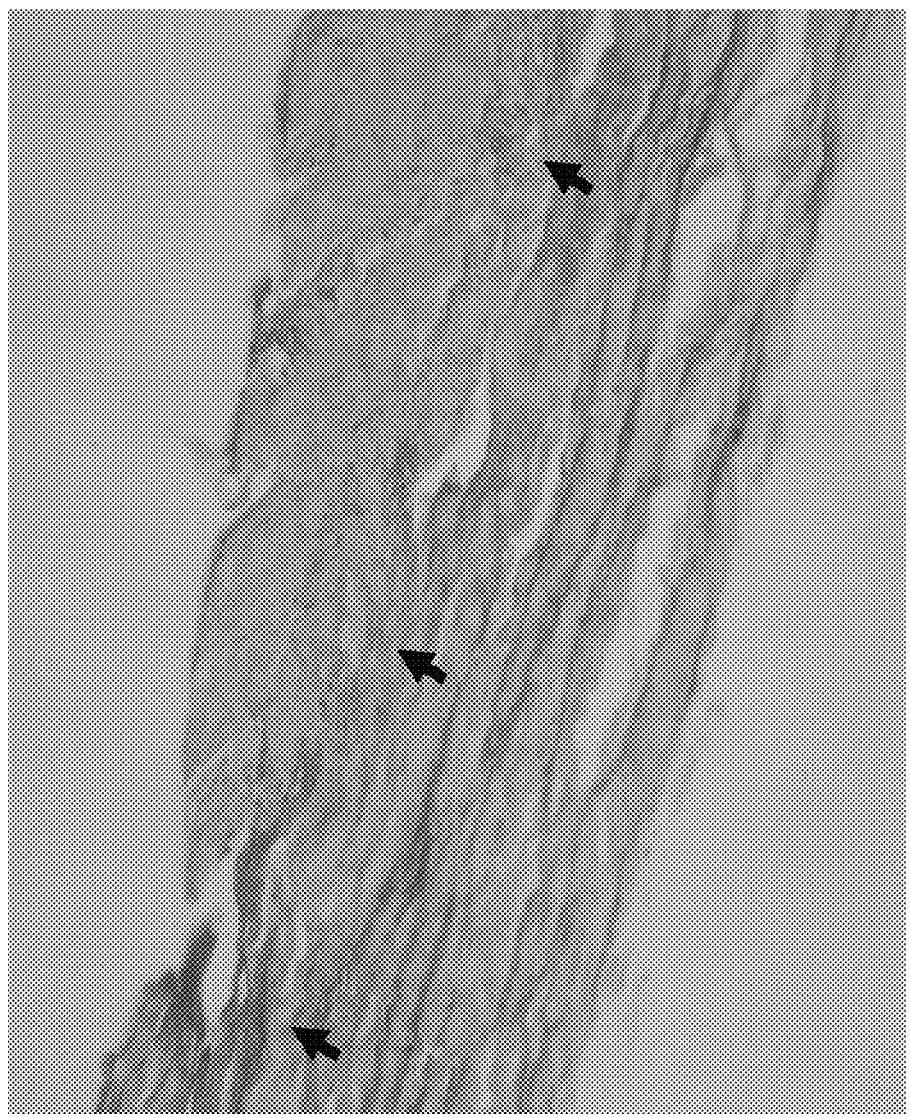
FIG. 2 is a histological cross-section of an adult bovine pericardial tissue stained for elastin exhibiting the desired characteristic of elevated elastin. Elastin stains darkly and is highlighted with the arrowheads.
Figure 3:
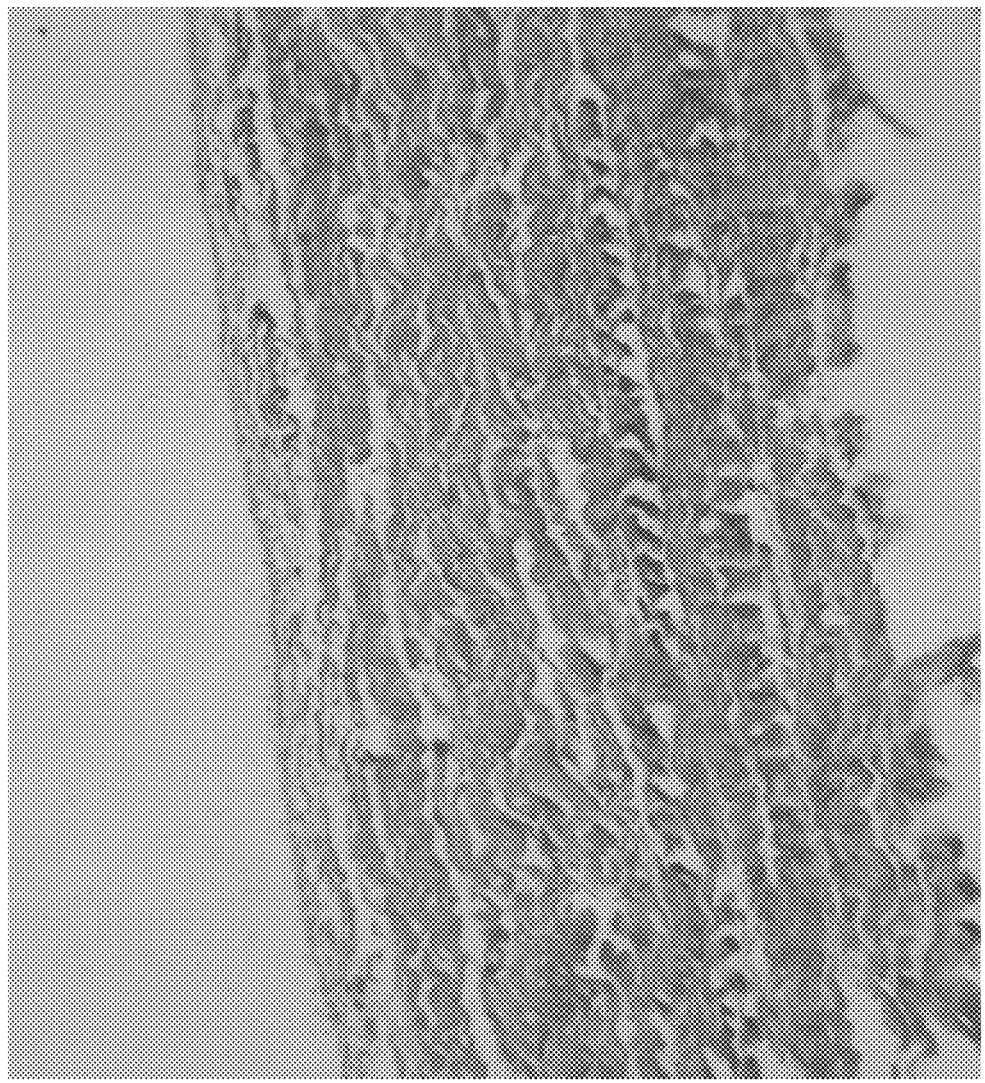
FIG. 3 is a histological cross-section of an adult bovine pericardial tissue stained for elastin which is typically used today for heart valve leaflets, patches, and soft tissue reconstructions. Note the general absence of elastin staining.

In another embodiment, adult bovine pericardial tissues are harvested from free-range fed cattle analyzed for the parameters and physical characteristics described herein and processed according to standard techniques. Through analysis and screening, elevated elastin levels, improved collagen characteristics and other desirable parameters can also be found in adult bovine animals, particularly when those animals are free-range fed (i.e., are allowed to graze on an open field for food), rather than fed in confinement at a feedlot. In contrast, prior art tissues are typically sourced from feedlot-fed animals, and these tissues have very low levels of elastin. As seen in FIG. 2, adult free-range fed cattle demonstrate extensive elastin fibers in pericardial tissue, while pericardium from feedlot-fed animals are low in elastin (see FIG. 3). Thus, even adult tissues of the embodiments described herein are improved over prior art tissues.

In a further embodiment, neonatal tissues rich in alternate collagen types could be used to provide specific advantages over prior art tissues. Preferably, alternate collagen types and parameters are measured and identified in combination with improved elastin characteristics or other qualities described herein. Neonatal or juvenile bovine pericardium is rich in altered collagen types, such as types II and III, while adult bovine pericardium is composed primarily of Type I Collagen. Type III collagen fibrils are smaller than Type I collagen fibrils and are crosslinked to the proteoglycans in the matrix by their association with Type IX collagen. Such interconnections can provide important stress-relieving mechanisms in a tissue which can help prevent tissue fatigue and degeneration. Vyavahare et al, *Mechanisms of bioprosthetic heart valve failure: fatigue causes collagen structural denaturation and glycosaminoglycan loss*, Journal of Biomedical Materials Research, volume 46, pp 44-50, 1999, report that progressive and marked depletion of glycosaminoglycans in the tissue matrix occurs after tissue flexing, and conclude that since glycosaminoglycans are largely responsible for tissue viscoelasticity and accommodation of the dynamic relationship between tissue layers, that removal of these glycans may be important in mechanically-mediated tissue degeneration.

Figure 4:
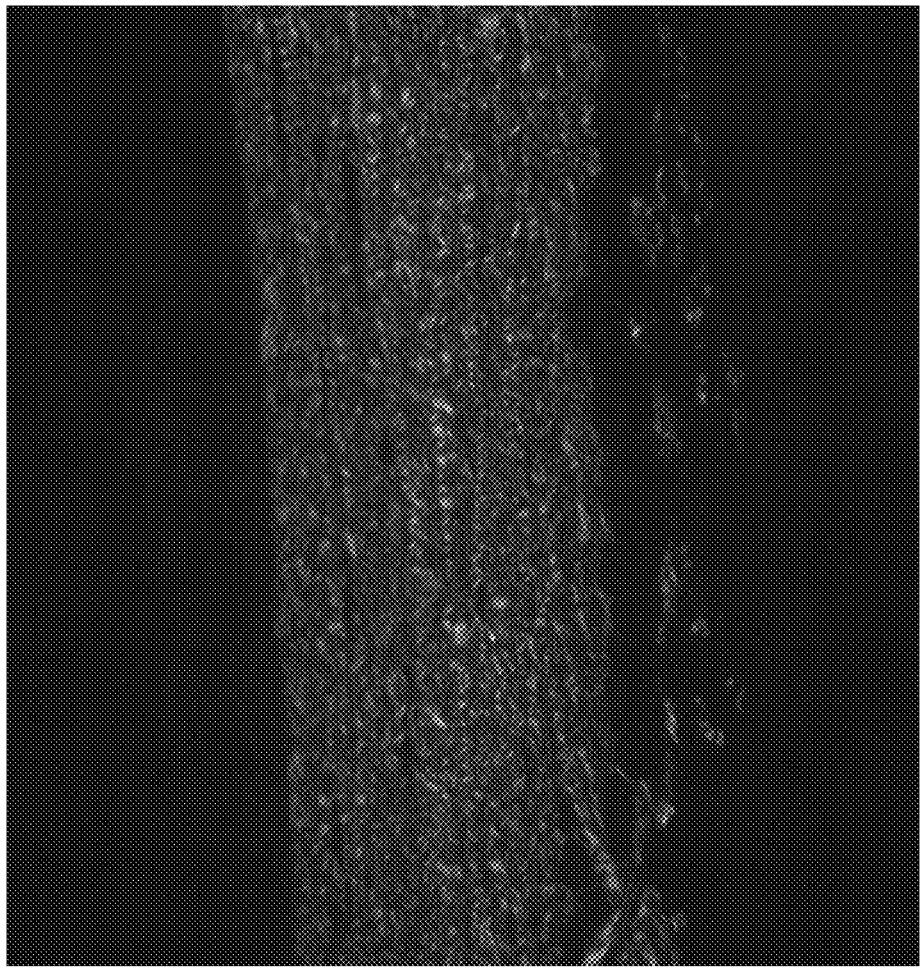
FIG. 4 is a histological cross-section of a neonatal bovine pericardial tissue stained with picrosirius red and viewed by polarized light.
Figure 5:
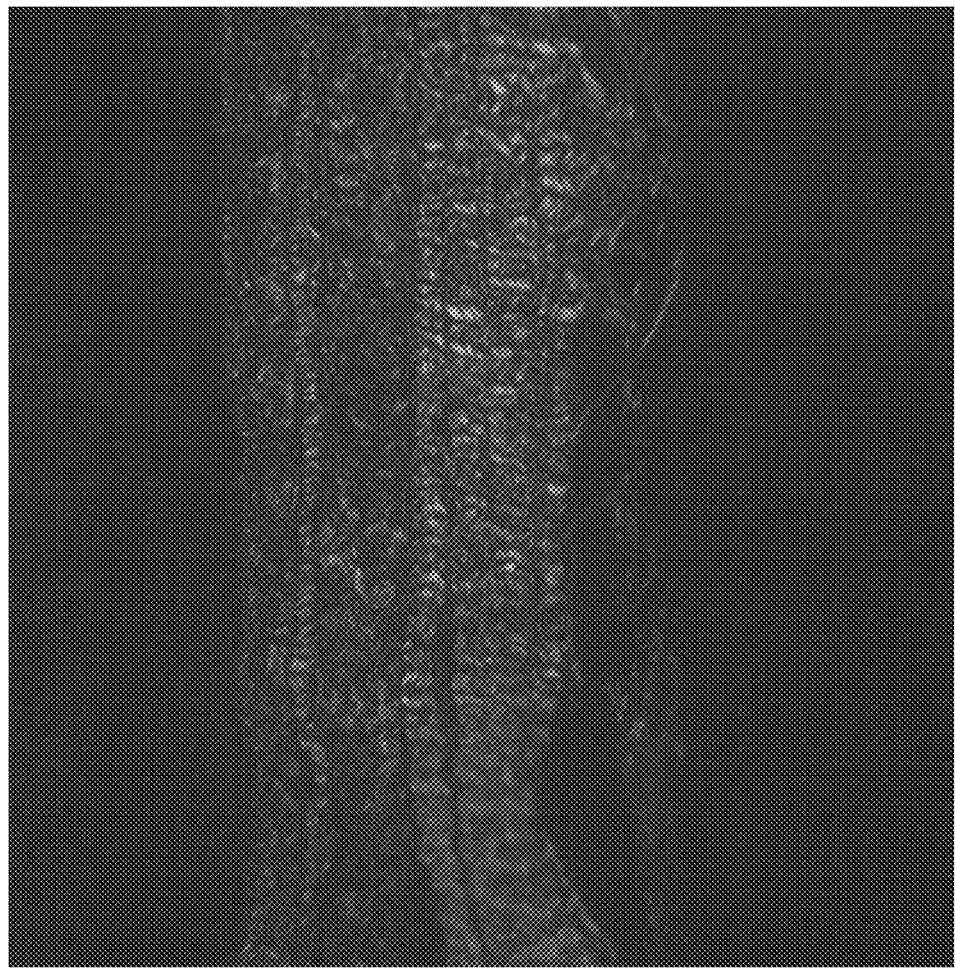
FIG. 5 is a histological cross-section of an adult bovine pericardial tissue from a free-range fed animal stained with picrosirius red and viewed by polarized light.
Figure 6:
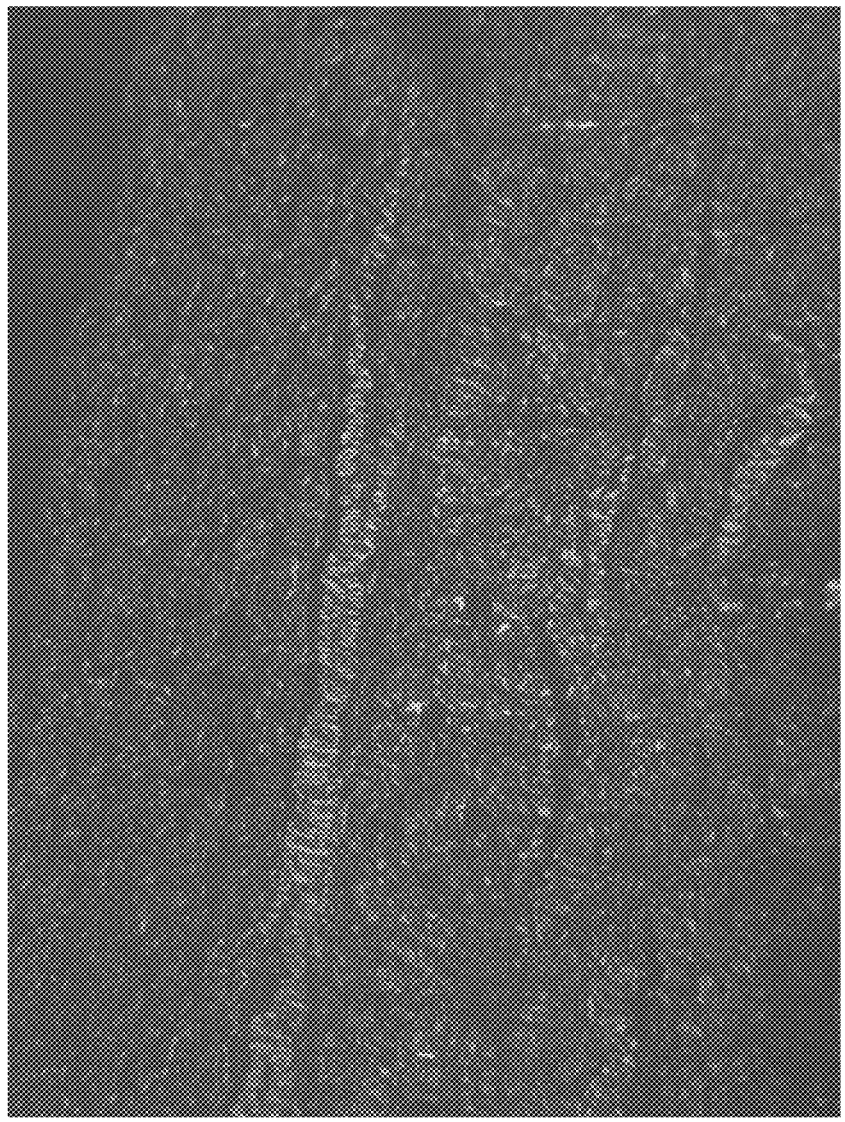
FIG. 6 is a histological cross-section of an adult bovine pericardial tissue from a feedlot-fed animal, stained with picrosirius red and viewed by polarized light.

FIG. 4 highlights the smaller collagen fibrils in the juvenile tissue when stained with picrosirius red and viewed under polarized light. FIG. 5 illustrates the larger collagen bundles in adult bovine pericardial tissues, which form distinct layers, with the fibers within one layer all running parallel to each other, and the layers oriented opposite each other, to provide resistance to expansion under load. FIG. 6 contains a histological cross-section of prior art adult bovine pericardial tissue, taken from an animal raised on a feedlot, stained with picrosirius red and viewed under polarized light. Because of the altered collagen subtypes in neonatal tissue, neonatal tissues may be more flexible and viscoelastic compared to the adult tissues, and thus exhibit improved durability.

Figure 7:
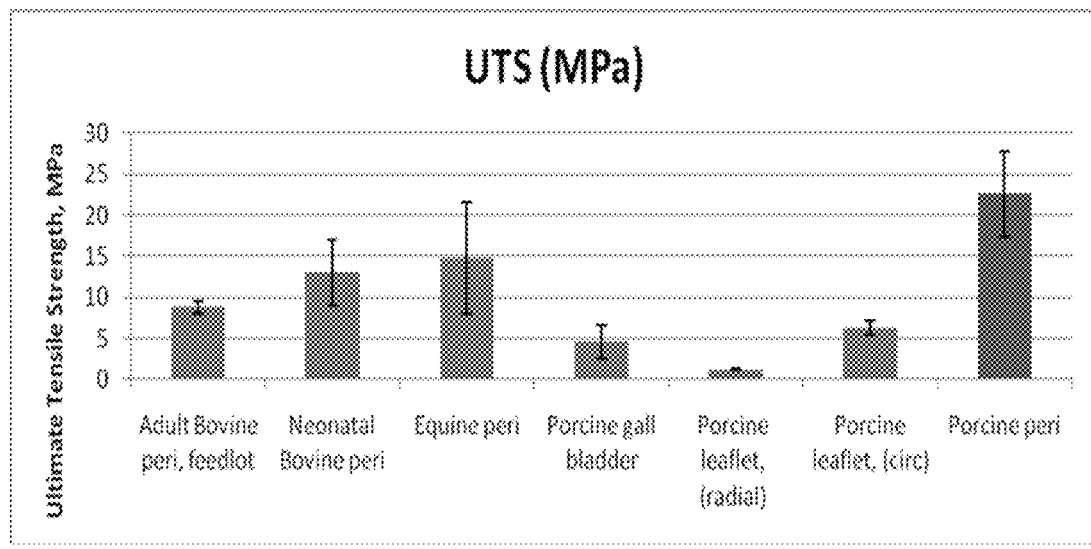
FIG. 7 is a graph showing the ultimate tensile strength of several ECM matrix materials used in cardiac replacement and soft tissue reconstruction, including adult bovine pericardial tissue typically used today in heart valve leaflets and patches, along with the ultimate tensile strength of neonatal bovine pericardial tissue exhibiting the desired characteristics of elevated elastin.

Strength is important as a measure of a desirable tissue and as a confirming property of the separate, desirable tissue characteristics described herein. FIG. 7 contains a graph of the ultimate tensile strength of a number of tissues used in tissue bioprostheses and soft tissue repair and reconstruction. In general, pericardium is an ideal choice for a strong tissue. Pericardium from any species is significantly stronger than other ECM tissues, such as gall bladder and native porcine aortic valve leaflets. Neonatal bovine pericardium is stronger than prior art adult bovine pericardium and is markedly thinner. Therefore, the use of neonatal bovine pericardium having the characteristics and properties described herein will enable stronger, more flexible, and more durable devices to be built, with distinct advantages over devices built with prior art tissues and processing technologies.

Figure 8:
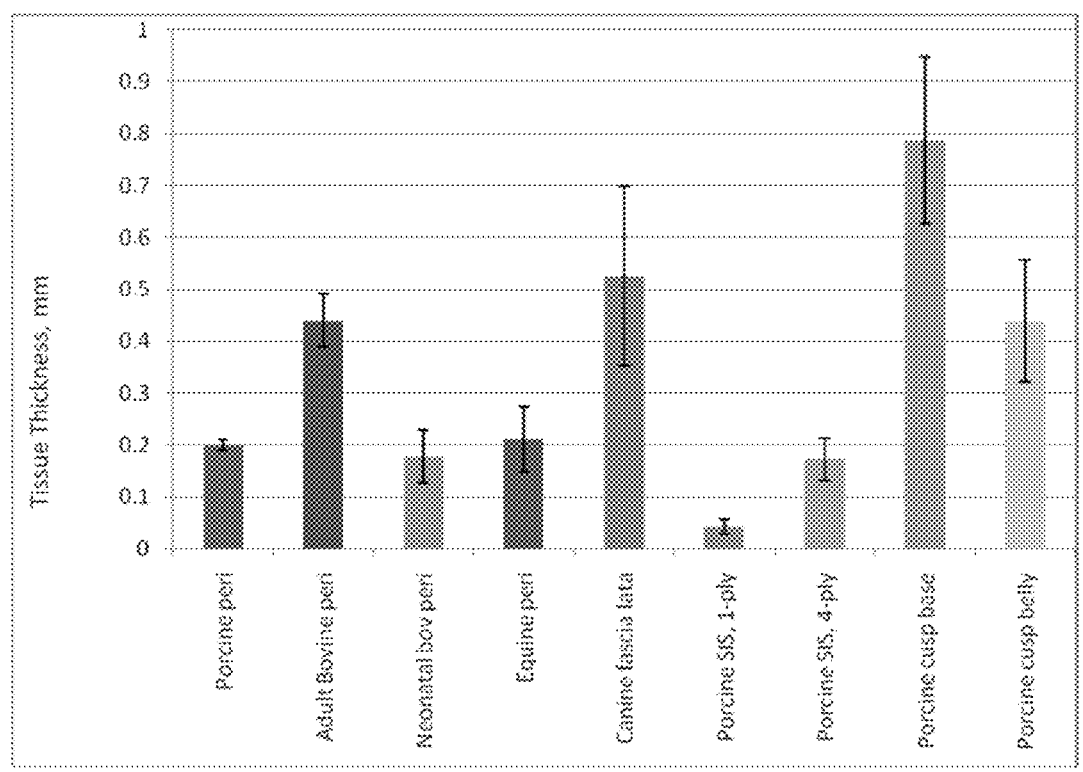
FIG. 8 is a graph showing the average thickness values for a range of fresh tissues used in heart valve leaflets, patches, and soft tissue reconstructions.

As described previously, tissue thickness is an important parameter in some applications, such as percutaneous tissue valves. As shown in FIG. 8, the various tissues used in soft tissue reconstruction have a wide variety of thicknesses. Neonatal bovine pericardium is the thinnest of the pericardial tissues, and a review of the strength of various tissues used in soft tissue reconstruction and cardiac replacement shows that pericardial tissues have the greatest strength of these materials. While porcine SIS tissue is thinner than neonatal bovine pericardium, it is not approved for use in soft tissue replacement, only soft tissue augmentation.

Figure 9:
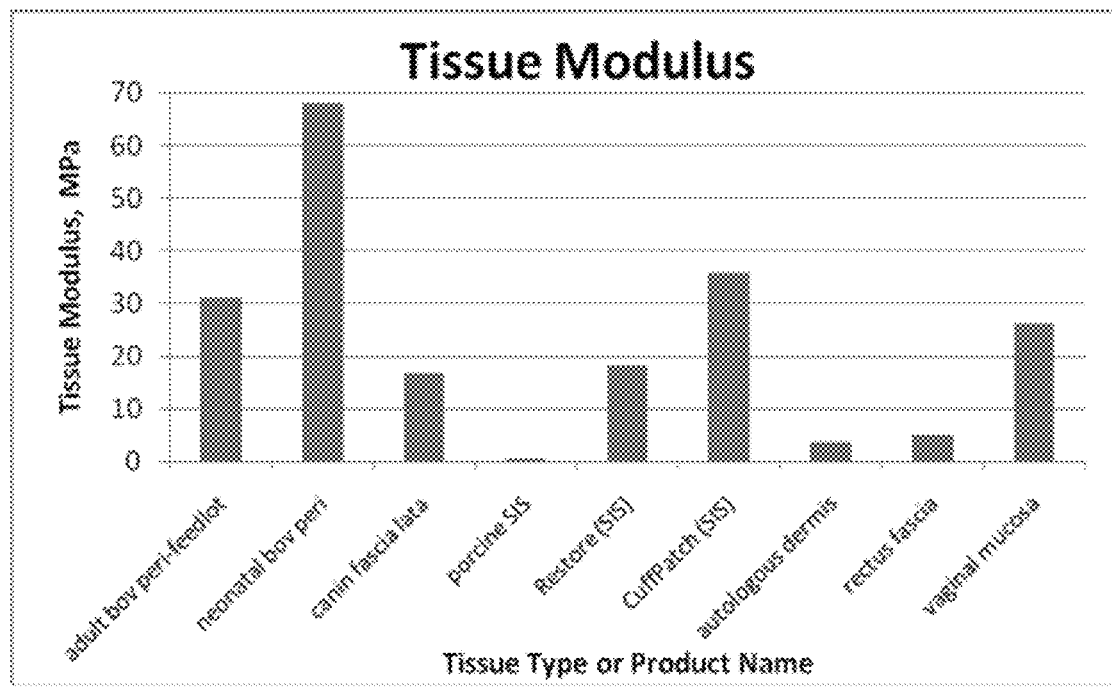
FIG. 9 is a graph showing average modulus values for a range of ECM matrix tissues used in cardiac replacement and soft tissue reconstructions.
Figure 10:
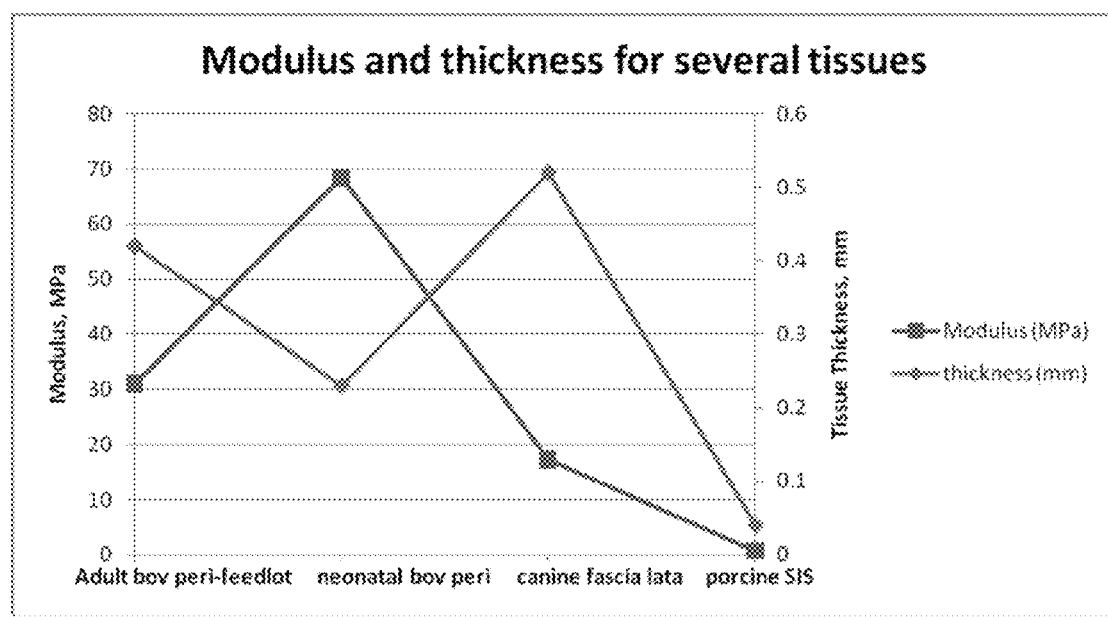
FIG. 10 is a graph of average thickness values and modulus for a range of tissues (as supplied) used in heart valve leaflets, patches, and soft tissue reconstructions.

FIG. 9 shows the modulus of several tissues used in soft tissue reconstruction. The data show that neonatal bovine pericardium has an unexpectedly high modulus, given its relative thinness. This surprising result is exemplified in FIG. 10, where tissue modulus and tissue thickness are graphed for each tissue type used in soft tissue reconstruction. Clearly the neonatal bovine pericardium characterized herein has enhanced properties relative to prior art tissues.

Without limiting the application of the embodiments described herein to currently existing devices, as the embodiments described herein will undoubtably enable the creation of new, currently-unimagined devices, several examples are illustrative of the advantages of the embodiments described herein over the prior art.

Example 1

Percutaneous Bioprosthetic Heart Valves

As discussed previously the advantages of neonatal bovine pericardium over the prior art lies in the increased elastin content, altered collagen types, and ultra-thinness which, taken together, allow the successful creation of minimally invasive percutaneous heart valve technologies with enhanced durability and improved hemodynamics, compared to the prior art. Such a device is fabricated from sourcing neonatal bovine pericardial tissues from juvenile animals, 1 year of age or less, and preferably less than 6 months old, less than 3 months old, and/or less than 30 days old. Even more desirably, the device is fabricated from neonatal bovine pericardium sourced from animals which are 30 days old or less and that exhibit the characteristics and properties defined herein.

The process by which the tissue characteristics and parameters of the present invention are utilized can vary depending on the ultimate use of the tissue and/or the device in which the tissue will be used. Also, depending on the harvesting techniques for the particular tissue, the tissue characteristics and parameters can be used as a quality assurance/quality control process, a tissue selection and verification criteria, or a method to identify populations of animals, species of animals, or subspecies of animals, exhibiting desirable tissue characteristics for the biomaterial applications described herein. Accordingly, a tissue source for heart valves may use the specific biochemical characteristics and parameters described herein as a selection criteria for each source tissue selected during a tissue harvesting process. Similarly, a tissue source may use the parameters described herein as a technique to locate populations of animals based on species or location that have a significant tendency to exhibit the desirable physical and biochemical parameters described herein. Finally, where individual tissues are destined to be utilized in devices such as heart valves, the specific biochemical and strength parameters disclosed herein can be used to match tissue types to specific applications, can be used to match tissue sources for use in a single device, i.e. matching heart valve leaflets to select materials having specific physical and chemical properties or to match specific physical and chemical properties from among different tissue types or samples. As described in more detail below, the measurements of the specific parameters as described herein can be used together with conventional chemical processing technologies that improve the stability or lessen the immunogenicity or bioburden of the tissues when harvested. Otherwise, the harvesting and chemical processing techniques available for use with the tissues and methods of the present invention are known to those of ordinary skill in the art. Generally, after harvesting, the tissues are cleaned to remove any adherent fat and rinsed in isotonic buffered solution to wash away any residual blood. After cleaning, tissues may be shipped to an off-site manufacturing location for further processing.

The cleaned fresh neonatal bovine pericardial sacs are inspected for integrity and damage, and rinsed further to reduce any incoming bioburden. After this inspection and rinsing process, each tissue is laid out on a cutting board and large patches are isolated for fixation. Fixation can occur in a number of ways, including floating, retaining the tissue on a board and placing the board into a fixation bath, suspending the patch from a frame, or exposing the patch to a force, either in the uniaxial or biaxial direction.

The tissues are fixed in a dilute solution of isotonic-buffered glutaraldehyde, such as, e.g., 0.625% glutaraldehyde in isotonic phosphate buffered saline at pH 7-7.4. A preferred concentration of glutaraldehyde is in a range that does not introduce excessive stiffness into the material. It is known to those skilled in the art that dilute solutions of isotonic-buffered glutaraldehyde <1% concentration will not result in overly stiff tissue. Acceptable alternatives include concentrations of 0.5% glutaraldehyde, 0.3%, 0.25% and even 0.1% or less, provided crosslinking is allowed to progress to completion.

Once fixation is complete, fixed tissues should demonstrate an increase in shrinkage temperature. As described in detail by Loke and Khor, *Validation of the shrinkage temperature of animal tissue for bioprosthetic heart valve application by*

*differential scanning calorimetry*, Biomaterials, volume 16, pp 251-8, 1995, the shrinkage temperature of fresh porcine pericardial tissue is about 66° C., while the shrinkage temperature of glutaraldehyde-treated porcine pericardium is about 86° C. In the embodiments described herein, freshly isolated neonatal bovine pericardial tissues exhibited a shrinkage temperature of 65° C. while glutaraldehyde-fixed neonatal bovine pericardial tissues have a shrinkage temperature of 84° C. Shrinkage temperature is not a good measure for distinguishing differences between tissues, but it is useful to demonstrate that tissues have been crosslinked in glutaraldehyde.

Figure 11:
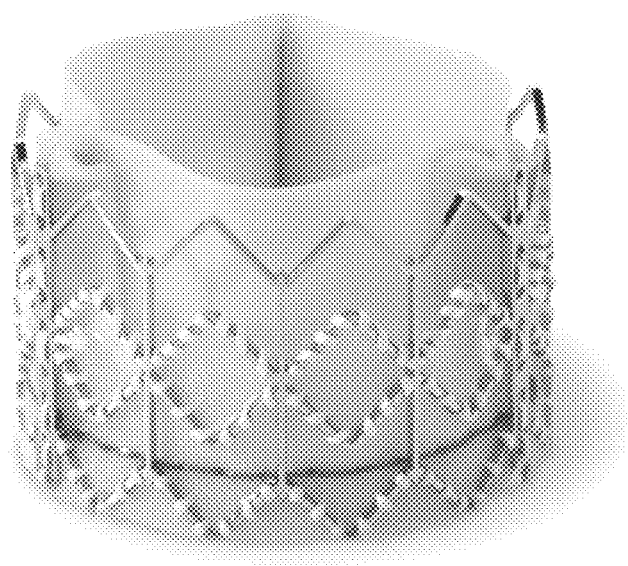
FIG. 11 illustrates a typical percutaneous heart valve, fabricated from prior art bovine pericardium.
Figure 12:
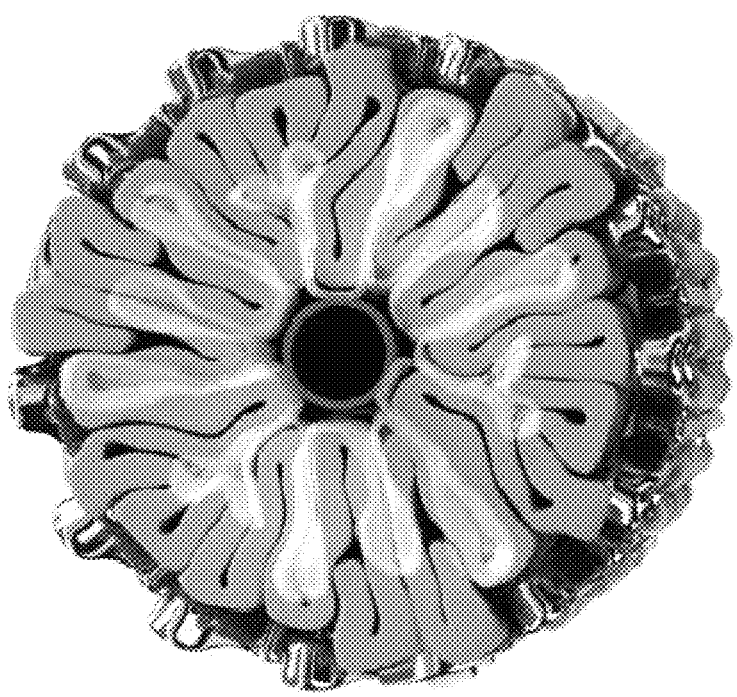
FIG. 12 shows the percutaneous valve when crimped for delivery. Note the large volume of space occupied by the tissue.

After fixation, leaflets may be cut from the tissue, using any harvesting method known to those skilled in the art. Leaflets are fabricated into valves through an assembly process which is specific to the valve design, but FIG. 11 contains an exemplary percutaneous valve design fabricated from prior art bovine pericardial leaflets. FIG. 12 contains an illustration of a percutaneous valve compressed for delivery, with an overall size of 22F, or 7.3 mm. Because the embodiments described herein uses neonatal bovine pericardium for the leaflets, which, as demonstrated in FIG. 8 are half the thickness of prior art adult bovine pericardium, the embodiments described herein can be compressed down to a smaller size, reducing the volume fraction of the tissue in the compressed state by as much as 60%. A significant reduction in tissue profile and volume enables the valve to be compressed into a 16F catheter or less, ensuring its delivery via the peripheral arterial system, which is the most minimally invasive means to deliver a percutaneous valve.

After delivery, the valve will demonstrate improved performance over valves made from prior art tissues. Not only is the implantation less traumatic for the patient, enabling faster recovery and fewer post-operative complications, but the use of ultrathin, flexible neonatal bovine pericardial tissue for the leaflets will enable the valve to perform better hemodynamically. For example, the valve can demonstrate improved opening and closing times, when viewed in an in vitro tester, see e.g. Kuehnel et al, *Opening and Closure Characteristics of Different Types of Stented Biological Valves*, Thoracic Cardiovascular Surgery, volume 54, pp 85-90, 2006, demonstrate the rather sluggish opening and closing behavior of prior art adult bovine pericardial tissues compared to native porcine aortic valve isolations. Consistently, the thicker bovine pericardial leaflets took longer to open, 22-31 ms, versus 12-15 ms for the native porcine aortic leaflet valves. Similarly, the thicker bovine pericardial leaflets took longer to close, 69-75 ms, compared to 59-66 ms for the aortic valve leaflets. The thinner nature of the neonatal bovine pericardial tissues of the embodiments described herein should improve the hydrodynamic performance of the valve and enable more rapid valve opening and closing. This performance improvement is due in part to the reduced thickness of the neonatal tissue, but also to its increased elastin content, and collagen specifics that facilitate the tissue returning to the original shape, thus closing faster.

Example Two

Traditional Surgical Valves

A second example of the utility of the embodiments described herein is in the application of these improved tissues to the development of traditional surgically-placed bioprosthetic heart valves. In this example, both neonatal and adult bovine pericardial tissues would be advantageous over the prior art, as well as the use of neonatal bovine aortic valve isolations.

In the case of the bovine pericardial heart valve, surgical valves can be fabricated using methods known to those skilled in the art, and as described above in example one. Further, these valves may be treated with a process to mitigate calcification of the tissue, as reducing calcification is a key objective in obtaining a more durable, long-lasting surgical valve. For example, one such calcification mitigation treatment is to use AOA (alpha-amino oleic acid) as a capping agent to reduce reactivity of residual aldehydes after the glutaraldehyde fixation step. Such a treatment is described in Giradot et al, Prevention of Prosthesis Calcification, U.S. Pat. No. 4,976,733, issued Dec. 11, 1990, and is incorporated in its entirety. Other examples of suitable calcification treatments include those described by Nashef et al, Surfactant treatment of implantable biological tissue to inhibit calcification, U.S. Pat. No. 4,885,005, issued Dec. 5, 1989, now expired, and Cunanan et al, Enhanced phospholipid reduction and calcification mitigation of biological materials, US patent application 20040093674, published May 20, 2004, now abandoned.

As described previously, prior art bovine pericardial tissues isolated from animals raised on feed lots demonstrate reduced elastin levels, weaker UTS strength, and lower modulus, compared to the bovine pericardial tissues of the embodiments described herein, which contain high amounts of elastin and greater strength and modulus. These improved properties of the tissues from the embodiments described herein are able to extend the durability and longevity of valves made from these tissues, as discussed previously. Elevated elastin levels will lead to improved leaflet kinetics (quicker opening, closing times), reduced damage at points of bending, and reduced shear stress between the layers of the tissue, thereby resulting in increased longevity of the valve when made from tissues with these improved properties.

Another example of an improvement in surgical valve technologies over the prior art is the ability to provide native bovine aortic valve isolations in sizes that are typically smaller than those obtained from typical porcine aortic valve isolations. Because of the inherently smaller sizes of the neonatal calves used in the embodiments described herein, a wide variety of tissues with enhanced properties can be isolated, such as the native bovine aortic valve. In a manner similar to the fabrication of a porcine aortic valve, a neonatal bovine aortic valve may be used to fabricate a surgical valve. For example, after harvesting, the valve is trimmed down to isolate the tissue, rinsed extensively in isotonic neutral buffered salts solution, and fixed in glutaraldehyde to crosslink the tissues. Such preparations are known to those experienced in the art of bioprosthetic valve fabrication, and are included here. The glutaraldehyde-fixed bovine aortic valve isolation can be fixed onto a stent or frame, or processed as a stentless valve, using the original bovine aortic tissue. Such valves can be treated with optional calcification mitigation treatments, e.g., FET, as described above. Because of the inherently small sizes of the neonatal bovines, aortic valves of the size 20 mm or less can be easily fabricated, while it is extremely difficult to fabricate such small diameter valves from bovine pericardium. Indeed valves may be isolated that are even smaller in diameter than 20 mm, and this can therefore be useful in pediatric cases of valve replacement, where frequently small-sized bioprosthetic valves are not available. In some cases, bovine venous valves have been utilized in cases of pediatric congenital deformities, but venous valves are inherently weaker than valves that have been isolated from the arterial tree of the vascular system, presumably due to the higher pressures and greater flow rates that an aortic valve experiences compared to a venous valve. The use of aortic valve isolations over venous valve isolations will lead to improved longevity and durability of these valves, which is particularly important in children and the elderly patient with a very small aortic root size.

Example Three

Patches with Improved Properties

A number of applications of the present invention yield improved tissues with enhanced properties of strength, durability, flexibility, and reduced thickness such that prior art tissues can readily be replaced if from an existing procedure or protocol. For example, a pericardial patch can be used for general surgical reconstruction in the heart, the vasculature, or in other organ systems such as the bladder, peritoneum, or abdominal wall where a requirement exists for flexibility strength, durability, and lack of immunogenicity. Such patches can be chemically crosslinked or simply disinfected, using techniques known in the art. Patches may be treated to alter their calcification properties, promote adhesion, or minimize adhesion, as required for the desired application. Patches may even be treated with two different treatments, for example with an adhesive surface on one side, and an anti-adhesive treatment on the other side. The adhesive surface is placed against the organ wall being repaired, while the anti-adhesive surface is exposed to the biological fluids around the organ. Such an anti-adhesive treatment could include heparin or synthetic hydrogel materials such as vinyl pyrrolidinone, poly-2-hydroxy ethyl methacrylate, or the like.

Patches may be adhered to the tissue or organ being repaired using sutures, staples, or the like. Patches may be applied through a small incision using minimally invasive techniques, or even through the vascular system, if the patch is to be used in the cardiovascular system. Patches made from materials of the embodiments described herein demonstrate improved mechanical properties, as detailed in FIG. 9. Yoder et al, *Nonlinear and anisotropic tensile properties of graft materials used in soft tissue applications*, Clinical Biomechanics, volume 25, pp 378-82, 2010, discuss the limitations with the current patch materials made from prior art methods. Such patches have low moduli which ultimately limits their usefulness in certain applications, such as in rotator cuff tendon augmentation, where the modulus of human intraspinatus tendon is about 84 MPa, while current patch materials have moduli that are much lower than this, ranging between 18 to 36 MPa. Neonatal bovine pericardium, as provided in the embodiments described herein, is a much better match for tendon repair and replacement, with a modulus typically greater than 68 MPa. Generally, for tissue portions selected for general use and specifically for prosthetic heart valves, the excised tissues have a modulus greater than 20 MPa, greater than 50 MPa, between 20 and 100, between 50 and 100.

Figure 13:
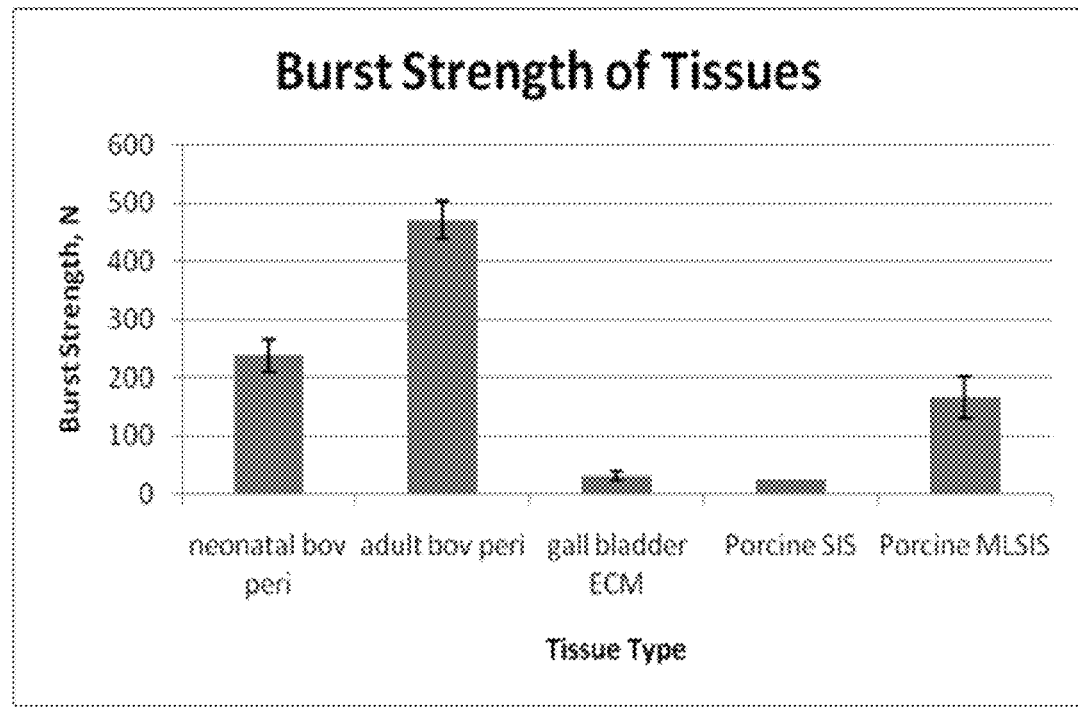
FIG. 13 graph of burst strength for a variety of highly oriented sample (b) tissues used in cardiac and soft tissue augementation and repair.

A further advantage to patches made with the embodiments described herein is the higher burst strength of these patches compared to traditional patch materials. FIG. 13 contains comparative data for a number of prior art tissues used for soft tissue reconstruction compared to tissues of the embodiments described herein. As is immediately evident, the tissues of the embodiments described herein are much more able to resist bursting in a controlled in vitro model used to objectively compare intrinsic material properties. In fact, either neonatal or adult bovine pericardial tissues are suitable, depending upon the thickness requirements of the patch application. Patches with elevated elastin levels are better able to resist burst forces and exhibit higher burst strengths compared to patches made from prior art tissues.

Example Four

Reinforcement Strips with Improved Properties

Figure 14:
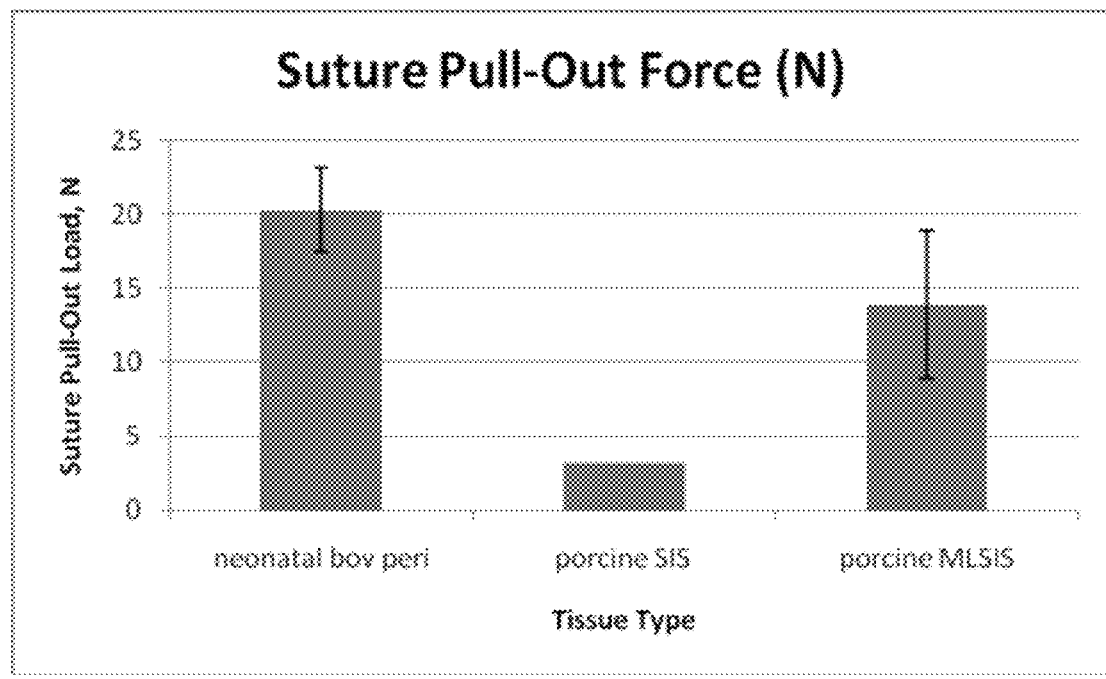
FIG. 14 is a graph of the suture pull-out force measured in a variety of tissues.

Because of the enhanced properties of tissues of the embodiments described herein, current devices can be fabricated with enhanced performance. For example, as described by Downey, Increased burst pressure in gastrointestinal staple-lines using reinforcement with a bioprosthetic material, Obesity Surgery, volume 15, pp 1379-83, 2005, strips of extracellular matrix materials (ECM) are helpful in gastrointestinal surgery, particularly in minimally-invasive procedures where staples are used. Including a strip of ECM material in the suture or staple area helps ensure integrity of the staple-line. The use of tissues from the embodiments described herein in such an application would further improve the burst strength of the reinforced wounds due to the enhanced properties of the present tissues compared to prior art tissues. As already shown in FIG. 13, the burst strength of tissues from the embodiments described herein is much greater than the burst strength of tissues from the prior art. Additionally, as detailed in FIG. 14, the suture retention strength of tissues from the embodiments described herein is greater than the suture pull-out strength of prior art tissues. These two factors together, improved burst strength and improved suture pull-out strength, will ensure a higher performance for reinforced sutures, staple-lines, and other mechanical interfaces where disparate mechanical properties can result in failure.

Figure 15:
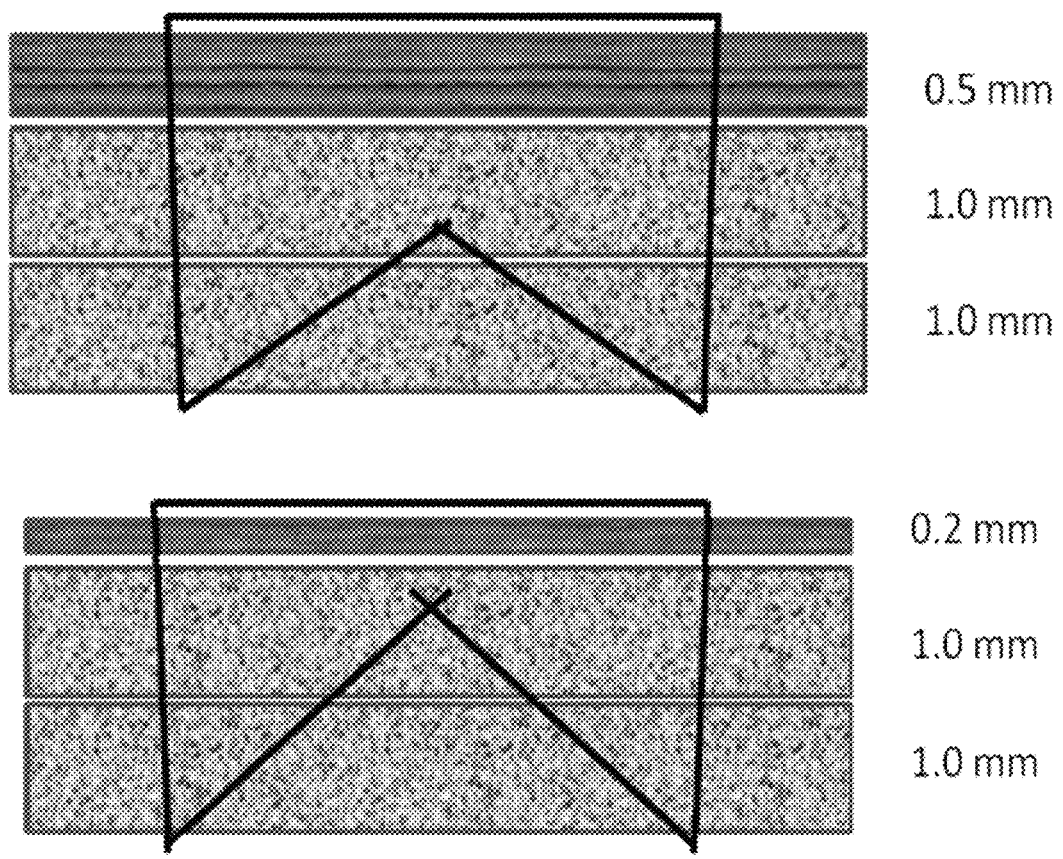
FIG. 15 is a set of illustrations comparing the use of a prior art tissue for staple line reinforcement compared to neonatal bovine pericardium, as described in the embodiments provided herein.

A further advantage of using tissues from the embodiments described herein in reinforcing sutures or staple-lines is that the neonatal tissue is much thinner than bovine pericardium from the prior art. Such reduced thickness helps ensure adequate room for staples to pass through the reinforcement strip and the tissues being joined and to 'bite back' to form a closed staple. Preferred thicknesses are between approximately 0.05-0.250 mm, and preferably between approximately 0.06-0.120 mm. As diagrammed in FIG. 15, the thinner neonatal pericardial tissue allows for a more consistent staple closure, therefore forming a stronger seal which should result in less postoperative leakage.

In the application of tissues from the embodiments described herein in patches, strips and other reconstructive uses, it should be well-understood by those skilled in the art that these tissues are not necessarily crosslinked with glutaraldehyde, but may be crosslinked with other more cell-friendly crosslinkers, such as EDC, or not crosslinked at all and simply disinfected with chemical means or irradiated for sterility. As such, crosslinking methods as described by Giradot et al, Method for fixation of biological tissue, U.S. Pat. No. 5,447,536, issued Sep. 5, 1995, and sterilization methods such as described by Giradot et al, Method of sterilization, U.S. Pat. No. 5,911,951, issued Jun. 15, 1999 are included in their entirety here.

Example Five

Improved Scaffolds for Tissue Engineering

Improved tissues of the invention can also be the foundation for tissue scaffolds used generally in tissue engineering. In the case of tissue engineered devices for pediatric applications, these living devices promise the potential of growth as the child grows, providing the ultimate in restorative therapies and correction of congenital and acquired abnormalities.

A typical tissue engineering process removes all cells from the original donor/host to avoid immunogenicity in the graft/transplant recipient. A representative decellularization procedure is described by Gilbert et al, *Decellularization of tissues and organs*, Biomaterials, volume 27, pp 3675-83, 2006). However, such decellularization techniques reduce the mechanical strength of tissue. Therefore, one of the advantages of this invention is maintaining mechanical strength after the decellularization process. In addition, because neonatal tissues are not fully crosslinked, removal of cells and other desired extractables can be done more easily while returning structural tissue elements (e.g. elastins, collagen), with less disruption to the tissue matrix. Therefore, use of tissues from the embodiments described herein will facilitate decellularization procedures and minimize the effects on loss of strength, when applied to the tissues in the invention.

A second consideration for a tissue engineered scaffold is whether or not the tissue should be crosslinked to prolong the lifetime of the tissue in the body. In many cases, the tissue is designed to be a permanent implant and to be resistant to degradation. In applications where a constant load or cyclic forces are applied, this might be most appropriate. In other applications it would be desirable to only temporarily stabilize the material, allowing the matrix to be resorbed as the cells repopulate and remodel the scaffold. An additional consideration for a scaffold material is the need for vascularization of the tissue to ensure the health of cells within the matrix. Scaffolds made from prior art materials are thicker than neonatal bovine pericardia from the embodiments described herein, and thus repopulation of these prior art scaffolds is reduced or inhibited due to nutrient starvation within the scaffold. Preparing scaffolds from neonatal bovine pericardium would not result in nutritional deprivation to incoming cells, because the tissues are ultrathin and therefore sufficient nutrients can pass through the material with simple diffusion.

Weind et al, *Aortic valve cusp vessel density: relationship with tissue thickness*, Journal of Thoracic Cardiovascular Surgery, volume 123, pp 333-40, 2002, performed a vessel analysis of porcine aortic valve cusps and found that the maximum diffusion distance for valve tissue is 0.2 mm. Accordingly, to avoid central ischemia in tissue engineered constructs, the scaffolds should not exceed 0.4 mm in thickness. Neonatal tissues easily meet this maximum thickness value, although prior art tissues are typically too thick to ensure adequate oxygenation of cells in the center of the tissues. Thus the reduced thickness of neonatal tissues provides another advantage over prior art tissues that will enable it to perform more optimally as a tissue engineered scaffold.

Example 6

Bovine Pericardium for Heart Valve Leaflet Replacement

Adult and neonatal bovine pericardium tissues fixed with gluteraldehyde were characterized by SAXS (Small Angle X-Ray Spectroscopy) to examine their microstructure. The adult pericardium has a statistically significant 0.20 nm longer d-spacing (65.82 nm) than neonatal pericardium (65.62 nm). Measured edge on to the tissue, Neonatal pericardium is significantly more aligned (OI vertical 0.80, horizontal 0.76) than adult pericardium (OI 0.58, 0.67). The more aligned fibrils with shorter spacing is the result of the altered collagen types in neonatal pericardium compared to adult pericardium. Type III collagen fibers are smaller and thus can be packed closer together, resulting in a greater density of collagen molecules per cross sectional area, greater strength, and greater alignment.

Heart valve leaflet replacement with calf pericardium may be performed through traditional surgical methods or percutaneously. Cribier, A.; Eltchaninoff, H.; Tron, C.; Bash, A.; Borenstein, N.; Bauer, E.; Derumeaux, G.; Pontier, G.; Laborde, F.; Leon, M. B., Percutaneous artificial cardiac valves: from animal experimentation to the first human implantation in a case of calcified aortic stenosis. *Arch. Mal. Coeur Vaiss.* 2003, 96, (6), 645-652. The procedure typically requires minimally invasive access to the patient's peripheral musculature, advancing a low profile catheter having the prosthetic valve releasably attached to the distal end thereof to traverse the vasculature to the heart where the diseased valve is removed and the prosthetic implant therein. The procedure is performed under direct or remote visualization using apparatus known in the art. See U.S. Pat. No. 7,381,219. Where the valve is placed percutaneously, the valve mechanism and any tissue components must be capable of assuming a low profile configuration so that the valve assembly can be releasably attached to the distal end of a catheter and advanced through a patient's peripheral vasculature, to the site of the heart where the valve is to be replaced. This procedure and the mechanisms necessary to accomplish it place special demands on the biochemical properties of the prosthetic valve and any tissue components thereof. Typically, the processed pericardium must be rolled tightly to be inserted. Increased strength and durability of the calf pericardium tissue with decreased size enable a smaller profile for the replacement prosthetic valve. The biomechanical properties of calf pericardium is directly related to the distribution and orientation of the collagen fiber bundle. Structure of collagenous tissues can be characterized by small angle X-ray scattering (SAXS) thereby yielding a quantitative measure of fibril orientation and of the collagen fibril d-spacing. Moreover, the structure of pericardium from adult cattle and neonatal cattle may be quantified and also analyzed for desirable physical properties to simulate the procedure required for percutaneous insertion.

To demonstrate the desired physical parameters, samples of pericardium were processed and fixed with glutaraldehyde from 10 adult and 10 neonatal cattle. Strips were cut in two directions perpendicular to each other. Replicates of each sample were provided, with one set rolled tightly and the other left unrolled.

After soaking for at least one hour in buffered saline solution (pH 6.8, 0.01% NaCl) the strips were mounted between 7 μm thick kapton tape (to retain the samples in a wet state). The X-ray beam was directed either through the flat surface of a sample or through one of two edge mounted samples so that for each material spectra were recorded in each of three orthogonal directions through the tissue.

Diffraction patterns were recorded on the Australian Synchrotron SAXS/WAXS beamline, utilizing a high-intensity undulator source. Energy resolution of $10^{-4}$ is obtained from a cryo-cooled Si(111) double-crystal monochromator and the beam size (FWHM focused at the sample) was 250×80 μm, with a total photon flux of about $2\times10^{12}$ ph·s$^{-1}$. All diffraction patterns were recorded with an X-ray energy of 12 keV using a Pilatus 1M detector with an active area of 170×170 mm and a sample to detector distance of 3371 mm. Exposure time for diffraction patterns was 1 s and data processing was carried out using the SAXS15ID software.

The d-spacing was determined for each spectrum from Bragg's law by taking the central position of several of the collagen peaks, dividing these by the peak order (usually from n=5 to n=10) and averaging the resulting values. The orientation index (OI), is defined as (90°—OA)/90° where OA is the minimum azimuthal angle range that contains 50% of the microfibrils. OI is used to give a measure of the spread of microfibril orientation (an OI of 1 indicates the microfibrils are completely parallel to each other; an OI of 0 indicates the microfibrils are completely randomly oriented). The OI is calculated from the spread in azimuthal angle of the most intense d-spacing peak (at around 0.059-0.060 Å$^{-1}$).

Figure 16:
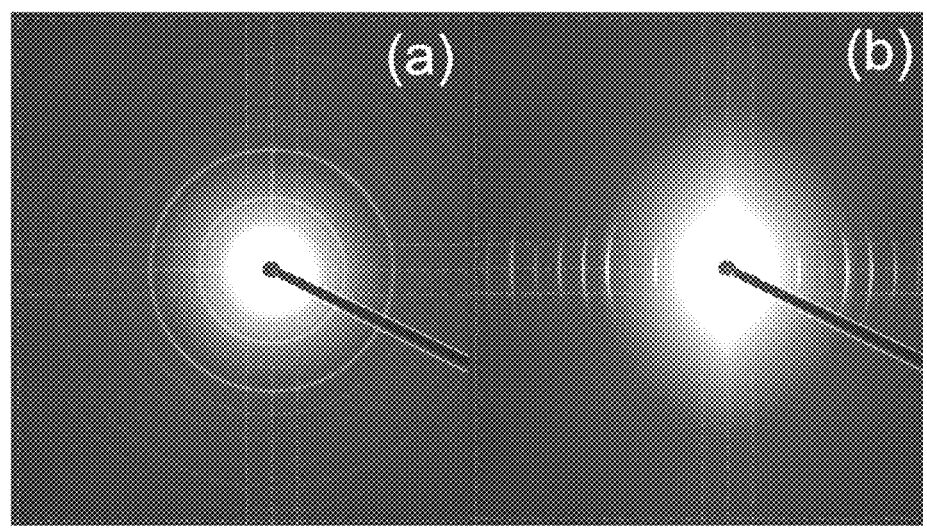
FIG. 16 is a SAXS spectra of pericardium samples showing a largely isotropic sample (a) and a highly oriented sample (b).

Referring to FIG. 16, two selected SAXS images are shown in illustrating an isotropic sample (a) and a highly oriented sample (b). This difference is reflected in the orientation index (OI). The d-spacing is represented by the distance of the rings from the centre of the beam, with multiple rings representing various harmonics of the collagen d-spacing.

A clear difference was observed between the d-spacing of the adult and the neonatal pericardium tissue (Table 1). The adult pericardium has a 0.20 nm shorter d-spacing of 65.82 (0.11) nm than neonatal pericardium of 65.62 (0.25) nm. A t-test on the difference between these two tissue types shows that this difference is statistically very significant (t-stat=7.2, P=2×10$^{-10}$).

However, rolling of the tissue does not alter the d-spacing of the tissue at all with a very close match between the d-spacing of the rolled or not-rolled pericardium (Table 1).

TABLE 1 d-spacing of pericardium

|  | Avg d-spacing (nm) | std deviation | no. of pericardia | no. of measurements |
|---|---|---|---|---|
| Not rolled: |  |  |  |  |
| Adult | 65.82 | 0.11 | 10 | 42 |
| Neonatal | 65.62 | 0.14 | 10 | 42 |
| Rolled: |  |  |  |  |
| Adult | 65.82 | 0.25 | 10 | 43 |
| Neonatal | 65.61 | 0.13 | 10 | 40 |

The collagen fibrils measured flat onto the tissue is very small, meaning the fibrils are almost isotropically arranged. There is a slightly greater alignment for adult tissue OI=0.020 than for neonatal tissue OI=0.071 (Table 2) although this difference has a weak statistical significance (t-stat=−0.794, P=0.4296). After the tissue has been rolled there is a small increase in OI for both tissue types (adult t-stat 0.7098, P 0.4799; neonatal t-stat 1.481, P 0.1426), indicating the fibrils become more aligned, and the difference between adult and neonatal pericardium becomes more significant (t-stat=−1.996, P=0.4947).

TABLE 2

Orientation index for pericardium samples measured normal to the surface (flat)

|  | OI | no. of pericardia | no. of measurement |
|---|---|---|---|
| Not rolled: |  |  |  |
| Flat adult | 0.020 | 10 | 42 |
| Flat Neonatal | 0.071 | 10 | 42 |
| Rolled: |  |  |  |
| Flat adult | 0.051 | 10 | 43 |
| Flat neonatal | 0.199 | 10 | 40 |

In contrast to the flat measurements, edge—on the fibrils are more oriented and give a higher OI. The fibrils are therefore approximately in isotropic layers stacked one upon the other. However, there are marked differences between the neonatal and the adult pericardium tissue, and these differences are most noticeable in the degree with which these layers intertwine with each other.

Edge-on the adult pericardium tissue has a statistically significant lower OI than the neonatal tissue measured both in the vertical and the horizontal directions (vertical t-stat −21.458, P<1×10$^{-10}$, horizontal t-stat −4.375, P<5.856×10$^{-5}$) demonstrating that the fibrils in the neonatal tissue are significantly more aligned within the plane of the tissue than those in the adult tissues.

Rolling of the pericardium has little effect on the fibril orientation in the direction measured edge-on, except perhaps for the neonatal pericardium measured edge-on in the horizontal where a decrease in OI was recorded (a reduction in alignment).

TABLE 3

Orientation index for pericardium samples measured edge-on to the surface.

|  |  | OI | stdev | no. of measurements |
|---|---|---|---|---|
| Not rolled |  |  |  |  |
| Edge Vertical | adult | 0.581 | 0.051 | 52 |
| Edge Horizontal | adult | 0.669 | 0.032 | 27 |
| Edge Vertical | neonatal | 0.800 | 0.031 | 30 |
| Edge Horizontal | neonatal | 0.763 | 0.106 | 27 |
| Rolled |  |  |  |  |
| Edge Vertical | adult | 0.585 | 0.103 | 36 |
| Edge Horizontal | adult | 0.662 | 0.136 | 44 |
| Edge Vertical | neonatal | 0.803 | 0.083 | 29 |
| Edge Horizontal | neonatal | 0.668 | 0.064 | 24 |

Example 7

Compositional Analysis of Bovine Pericardium

Calf pericardium tissue is fundamentally different from adult tissue in ways that have direct application for heart valve and tissue graft performance. Calf pericardium tissue contains less fat and more nitrogen than adult tissues. See Table 3. It has a similar water content and higher DNA content: a) Less Fat means that the tissue may have fewer lipids to attract and bind calcium. Fat also consumes bulk without adding strength; b) More Nitrogen means the bobby tissue has a higher content of protein, which is the most likely source of the nitrogen; c) Similar water content. Both tissues have similar water contents, around 80%; and d) Higher DNA content which reflects the higher number of cells in the bobby tissue compared to adult tissue.

TABLE 3

| Tissue: | Fat Content (%) | Nitrogen (%) | Water content (%) | DNA content (mg/gr dry wt) |
|---|---|---|---|---|
| NZ neonatal | 0.6 | 14.7 ± 0.3 | 84.4 ± 1.0 | 3.9 ± 0.7 |
| NZ Adult | 2.1 ± 1.0 | 14.2 ± 0.3 | 79.3 ± 0.8 | 1.9 ± 0.4 |
| US Adult | 2.2 ± 2.2 | 13.9 ± 0.2 | No data | 1.9 ± 0.3 |

As noted above, calf pericardium tissue has a higher elastin content compared to adult tissue. Quantitative biochemical testing may measure two aspects of elastin composition. Both methods demonstrate a significant increase in elastin in calf tissues compared to adult tissues: a) Elastin content by colorometric assay; b) Desmosine content by HPLC.

Preferred elastin contents are greater than 0.025 micrograms per milligram dry weight, between 0.40 micrograms and 1.00 micrograms per milligram dry weight and between each lower range value and up to 0.75 to 1.0 micrograms dry weight. Desmosine/isodesmosine are the naturally-occurring crosslinks that occur in elastin formation; c) Elastin/Desmosine ratio demonstrates relative amounts (ug/ug) elastin versus desmosine, as an indicator of elastin crosslinking. See Table 4. Loss of desmosine crosslinks has been noted in tissue degeneration and aging.

TABLE 4

| Tissue: | Elastin content: (ug/mg dry wt) | Desmosine: (ug/mg protein) | Elastin/Des Ratio: |
|---|---|---|---|
| Glut-fixed Calf | 366 ± 40 | 0.58 ± 0.21 | 624 |
| Glut-fixed Adult | 267 ± 23 | 0.36 ± 0.29 | 746 |

Another biochemical compositional difference is noted in the amino acid analysis of these two tissues: d) Hydroxyproline/proline (HYP/P) ratio: Amino acid compositions are known to be different in tissues which contain predominantly Type I collagen versus Type III collagen. One characteristic of these tissues is that tissues rich in Type I collagen, such as adult bovine pericardium, have a HYP/P ratio<1. Tissues rich in Type III collagen, such as calf pericardium, have a HYP/P ratio>1. Adult tissue has a HYP/P ratio of 0.8 while calf pericardium tissue has a ratio of greater than 1.0, greater than 1.3 and up to 2.0.

As noted in Example 6, glutaraldehyde-fixed neonatal bovine pericardium is more highly aligned compared to similarly-processed adult pericardium as measured by the Small Angle X-Ray Scattering (SAXS) technique.

It is considered highly desirable to have anisotropy in the material, which is similar to the native leaflet, where the large collagen fibers run circumferentially through the leaflets. The smaller, more aligned molecules in the calf pericardium tissue impart different mechanical properties to the tissue and Type III collagen imparts an increased stiffness even with reduced thickness of a tissue sample.

Figure 17:
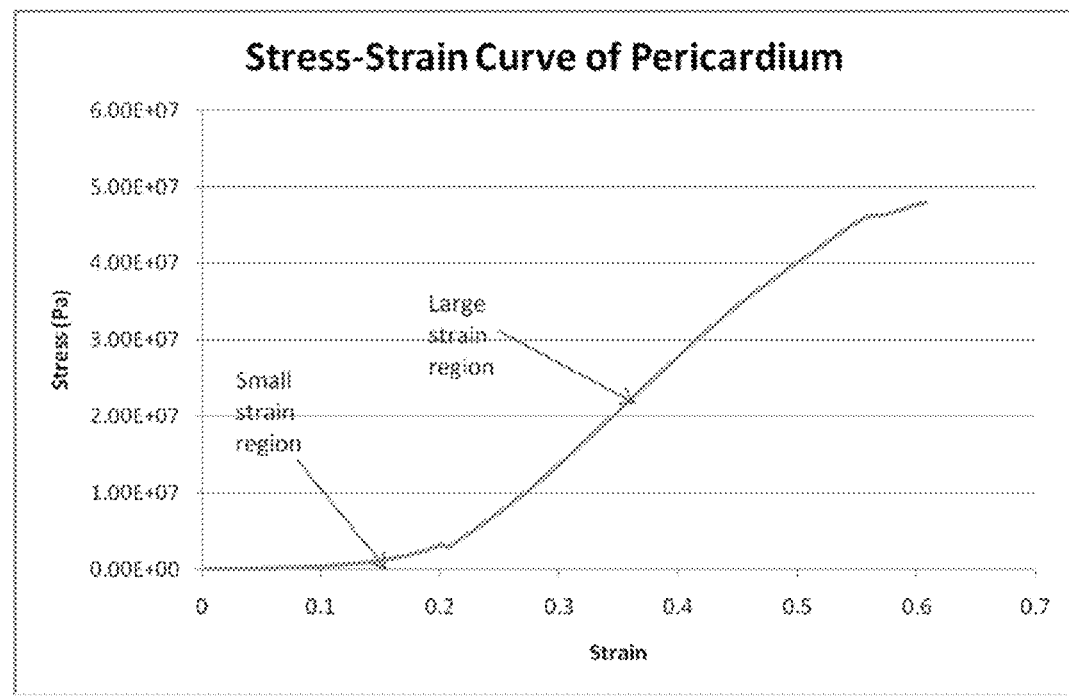
FIG. 17 is a stress (Pa) vs. strain curve for calf pericardium tissue.
Figure 18:
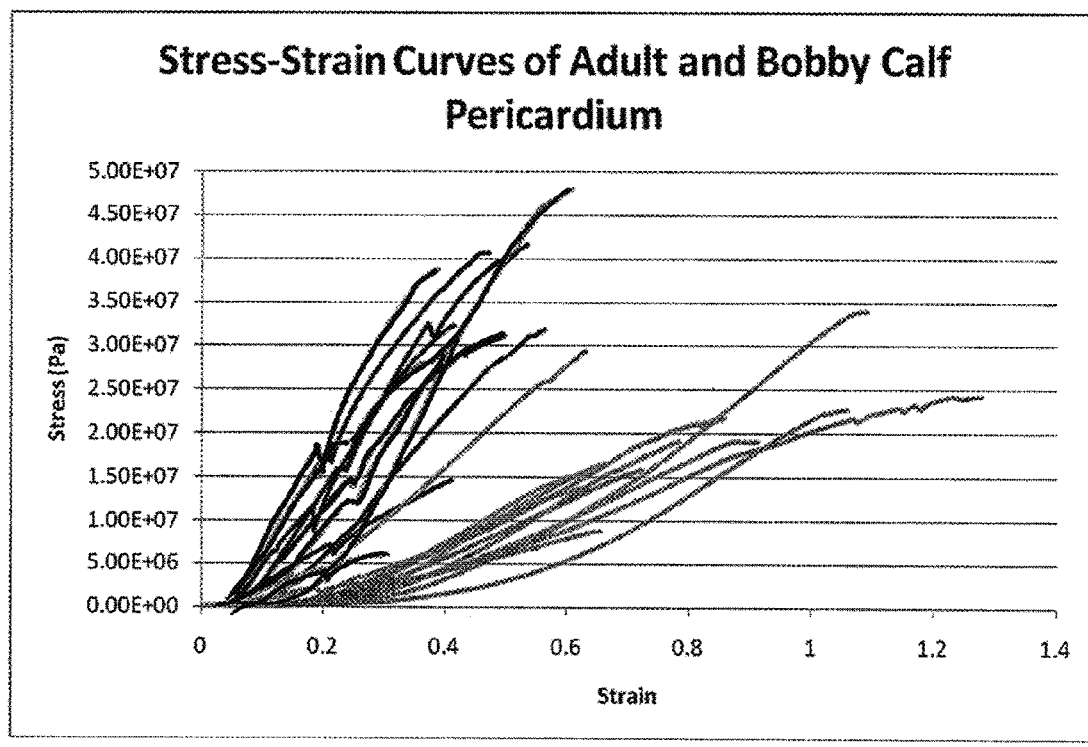
FIG. 18 is a composite of stress strain curves for multiple samples of calf tissue (upper distribution) and adult tissue (lower distribution).

Referring to FIG. 17, a stress-strain curve of a representative piece of pericardial tissue reveals a noticeably non-linear relationship in mechanical properties:

Referring to FIG. 18, a composite graph of the stress-strain curves of adult and calf glutaraldehyde-fixed pericardia shows a clear distinction with the upper population consisting of calf pericardium. The distinct differences between adult and calf pericardium tissue shows that adult tissues will elongate considerably under load, while the calf tissues demonstrate much less elongation under the same physical forces. Leaflets made from adult tissues can stretch during use, therefore not maintaining the intended shape of the valve. This change in leaflet shape can result in increased loads on the tissue with early degeneration, or in worst cases, the leaflets will fail to close shut entirely, leaving a central hole in the valve with constant backflow. Depending upon the amount of backflow, this condition can be fatal and always requires surgical reintervention.

A measure of the stiffness of the tissue is the slope of this stress-strain curve, also called the modulus. The slope of the line at low strain (<0.20) or at high strain (>0.20) demonstrates the increased stiffness of the neonatal tissue, making it more suitable for valve design, as it will be more likely to retain the shape of the valve during use.

The table below summarises results for adult and calf tissue and indicates significant differences in tissue properties between the two. Data are presented as mean (±standard error) with p values from a two-tailed t-test.

TABLE 6

| | Adult (n = 13) | Calf (n = 11) | p |
|---|---|---|---|
| Thickness (microns) | 358.72 (±25.92) | 119.72 (±6.13)* | <0.0001 |
| Normalised residual stress | 0.806 (±0.007) | 0.841 (±0.010)* | 0.0080 |
| Small strain† elastic modulus (MPa) | 4.77 (±1.99) | 71.9 (±11.6) | <0.0001 |
| Large strain‡ elastic modulus (MPa) | 33.5 (±3.19) | 83.7 (±10.6) | <0.0001 |
| Ultimate tensile strength (MPa) | 19.1 (±2.21) | 32.9 (±4.07) | 0.0050 |
| Strain at failure | 0.80 (±0.06) | 0.48 (±0.03) | 0.0002 |

*n = 12 for this measurement
†Modulus calculated for strain less than approximately 20%
‡Modulus calculated for strain greater than approximately 20%

Also included in the table above is the measurement of Ultimate Tensile Strength (UTS), which is the force required to break the material. Because of the smaller, more tightly packed fibers in the neonatal pericardium, it has a higher UTS compared to adult tissue. Note also that the adult tissues demonstrated higher strains at failure compared to the neonatal tissues, reflective of the greater extensibility of the adult tissue.

Example 8

Pepsin Solubilisation of Neonatal Calf Pericardium

The adult and neonatal neonatal tissue was solubilised with pepsin and dried and the weight of the remaining tissue is taken and values are given below:

| Pepsin digestion | % tissue remaining |
|---|---|
| Adult tissue | 21.1 (mean) |
| | 3.252 (STDEV) |
| Neonatal | 11.52 (mean) |
| | 0.294 (STDEV) |

The pepsin solubilisation assay results show that the adult pericardial tissue has more mature collagen crosslinks that are resistant to pepsin than the neonatal pericardial tissue (almost twice as much as neonatal). Generally, values between 9 and 15, and preferably between 10 and 13, are indicative of calf tissue.

As disclosed herein, Type I and Type III collagens are associated with different biochemical structural and mechanical properties. The data disclosed herein establishes that the neonatal tissues have better biomechanical properties than adult tissue, i.e., the collagen types are different. Due to the similarity in thicknesses of neonatal bovine and porcine pericardium, more collagen Type III is found in neonatal pericardium as porcine pericardium.

The presence of Type III collagen is strongly indicated by the amino acid data and the data suggest that differences in physical and biochemical properties between calf and adult tissue is explained by collagen orientation.

Example 9

Calf Pericardium Tissue Processing

The same processing parameters may be to process both calf pericardium tissues and adult tissues. Crosslinking with glutaraldehyde was assessed using Shrinkage Temperature and Amino Acid Analysis. Shrinkage Temperature (Ts) is a measure of the thermal stability of the material. Both adult and calf pericardium tissues treated with glutaraldehyde have an increase in shrinkage temperature and an increase in Ts that is generally considered to be synonymous with crosslinking.

An Amino acid analysis can be used to monitor the extent of the crosslinking reaction because glutaraldehyde reacts with the amino group in lysine. As the reaction progresses, the number of free lysines residues decreases, indicating that they have been crosslinked. Each measurement is normalized to an amino acid which does not participate in the reaction, to account for differences in the collagen content within a given sample. In this case, alanine is the non-reactive internal reference.

Table 7 shows the degree of crosslinking of each tissue type as a function of time:

TABLE 7

| Reaction Time (hrs): | Neonatal tissue (%): | Adult tissue (%): |
|---|---|---|
| 0 | 0 | 0 |
| 0.5 | 57 ± 11 | Not done |
| 3 | 60 ± 7 | 77 |
| 24 | 73 ± 3 | 77 |
| 48 | 75 ± 2 | 81 |
| 96 | 80 ± 1 | Not done |

The more dense matrix of the neonatal tissue may react slightly more slowly compared to adult tissue, but after several days exposure, the two tissue types have reacted similarly.

Example 9

Inhibition of Calcification

Despite the increased elastin composition of calf pericardium, higher calcification, which is the principal long-term failure mechanism of bovine pericardial valves, does not occur. Calcification was assessed by implanting glutaraldehyde-treated and fully-processed adult and neonatal bovine pericardia in the subcutaneous space in 28-day old Sprague-Dawley rats. After 30 days implantation, the specimens were retrieved and analyzed by histopathology and Calcium content was determined using ICP-MS.

Full process tissues demonstrated reduced calcification compared to glutaraldehyde-only controls. Referring to Table 8, adult tissues and calf pericardium tissues demonstrated similar levels of calcium in each process group.

TABLE 8

Calcium content, microgram Ca++/mg dry tissue weight

| Tissue Source: | Glut-only process: | Glut + FET process: |
|---|---|---|
| Adult | 19.1 ± 11.8 | 2.2 ± 4.5 |
| Neonatal | 17.8 ± 15.4 | 2.1 ± 6.0 |

These results indicate that, despite the differences in composition in neonatal tissues, higher levels of calcification not occur.

EXEMPLARY EMBODIMENTS OF CREATING TISSUES DESCRIBED HEREIN

As described throughout the previous examples, one means of creating tissues with the enhanced properties described is to identify populations of animals which produce tissues with those properties and to isolate tissues from these animals for use. Such harvesting of tissues and organs is typically done at an abattoir when the animals are taken for slaughter. As such, harvesting of tissues and organs which demonstrate these enhanced properties can be used to collect and ship these identified tissues and organs. These harvested tissues may be shipped in a solution of various compositions, including isotonic salts, buffered salts, or buffered salts with preservatives or osmotic control agents to protect the tissues during shipment.

Once received at the processing facility, tissues of the embodiments described herein are processed as previously described. Tissues may be sterilized using a variety of methods known in the art, including liquid chemical sterilants, heat or steam, gas, or ionizing radiation, such as e-beam or gamma irradiation.

While naturally-sourced neonatal bovine tissue is one mode for creating biomaterials with enhanced mechanical properties, other means of creating such tissues also exist. A logical extension of using tissues from younger animals is to use tissues from fetal sources. Fetal bovine tissues can be obtained during slaughter of adult cattle which are found to be pregnant. Additionally, fetal tissue could be obtained by first fertilizing a female cow some time prior to slaughter, ensuring a collection of fetal tissue in the process.

Genetically-engineered animals which express an abundance of elastin and collagen subtypes could be created through gene enhancement, by creating knock-out animals, through traditional breeding methods to enhance the desirable components, and other mechanisms known to those experienced in genetic manipulation. This manipulation could also be based on manipulating the expression of these desirable proteins, either in naturally-occurring animals, animals expressing the desirable proteins through random mutation, or those deliberately constructed or altered to exhibit enhanced protein compositions, such as through feed, environment, supplements, hormones and the like. Such genetically-engineered animals could provide materials of enhanced properties throughout the life cycle of the animal, such as an adult, a juvenile, or even a fetal animal, could provide tissues with enhanced material properties.

Cultures of cells could be created to express these proteins, and these proteins are then combined to form sheets, tubes, or other forms, which exhibit these enhanced properties. The cultures of cells could be obtained from natural sources, such as neonatal calf tissues, fetal calf tissues, genetically-manipulated adult tissues, or the like. Further, these cultures of cells could be genetically modified or manipulated to enhance expression of these desirable proteins, which are then fashioned into a device. These cultures of cells could be mammalian-derived, or bacterial-derived, and therefore having the desired mammalian genes introduced into them for the purposes of synthesizing the desired proteins and their subsequent fabrication into the desired device shape and composition. These cultures of cells could express those genes in abundance that are desirable, and from any source that is desirable, for example, overexpression of human elastin and collagen in mammalian or bacterial cells. Even more desirable, these cultures of cells could create the three dimensional shape of tissues, such as in sheets, tubes, or the like, with enhanced expression of desirable proteins within the cultures themselves. Such in vitro generation of constructs could be done by seeding cells displaying the desired expression profile onto surfaces or within scaffolds, forms, or other type of molds, such as is commonly used in tissue engineering. Finally, cells exhibiting the desired expression of proteins could be recombined to form three-dimensional shapes using 3-D scaffolding technology, as is commonly used in tissue engineering. All manner of creating cells, manipulating cells and/or recombining cells to result in three-dimensional constructs which have enhanced properties compared to such devices created with adult tissues and cells, are hereby contained within the parameters of the embodiments described herein.

While the invention is susceptible to various modifications, and alternative forms, specific examples thereof have been shown in the drawings and are herein described in detail. All references are specifically incorporated herein in their entirety. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A method to process calf pericardium tissue for human implantation comprising:

excising a portion of calf pericardium tissue from an animal less than 12 months old, sizing the tissue to be fashioned into a construct for implantation in a human patient, testing the tissue to measure an elastin content of greater than 326 micrograms per milligram dry weight, testing the tissue to measure a ratio of hydroxyproline to proline greater than 1.0, selecting tissue portions having the elastin content greater than 326 micrograms per milligram dry weight and the ratio of hydroxyproline to proline greater than 1.0 for use in human implantation as a dural patch or component of a prosthetic heart valve, and wherein the selected tissue portions are chemically treated to synthetically cross-link amino acid residues in the tissue portions to reduce immunogenicity.

2. The method of claim 1, further comprising the step of sizing the tissue portion to be used as the prosthetic heart valve or portion thereof.

3. The method of claim 1, wherein the synthetic, chemical cross-linking step comprises exposing the tissue to glutaraldehyde.

4. The method of claim 1, further comprising the step of measuring a thickness of the treated tissue and selecting those portions with a thickness of approximately 0.05 to 0.250 mm.

5. The method of claim 1, further comprising the step of determining that calf that is a source of the pericardium tissue is less than 30 days old.

6. The method of claim 1, further comprising the step of assaying the tissue by pepsin solubilisation before the chemical treatment step.

7. The method of claim 6, further comprising the step of selecting for chemical treatment only those portions with a residue after digestion of less than approximately 12% of original weight.

8. The method of claim 1, wherein the glutaraldehyde is isotonically buffered.

9. The method of claim 1, further comprising the step of measuring the Orientation Index of the tissue portion and selecting tissue portions with a Horizontal Edge Orientation Index greater than 0.75.

10. The method of claim 1, further comprising the step of determining the mechanical strength of the tissue portions and selecting those tissue portions with an Ultimate Tensile Strength greater than 20 MPa.

11. A tissue portion produced by the method of any of claims 1-3, 4-5 and 6-10.

* * * * *